(12) United States Patent  (10) Patent No.: US 8,840,668 B1
Donahoe et al.  (45) Date of Patent: Sep. 23, 2014

(54) SPINAL IMPLANTS, INSTRUMENTS AND RELATED METHODS

(75) Inventors: Ryan Donahoe, San Diego, CA (US); Shaeffer Bannigan, Carlsbad, CA (US); Benjamin Arnold, San Diego, CA (US); Andrew Schifle, Superior, CO (US); Michael Brotman, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 49 days.

(21) Appl. No.: 12/945,789

(22) Filed: Nov. 12, 2010

Related U.S. Application Data

(60) Provisional application No. 61/260,396, filed on Nov. 11, 2009, provisional application No. 61/389,956, filed on Oct. 5, 2010, provisional application No. 61/328,115, filed on Apr. 26, 2010.

(51) Int. Cl.
*A61F 2/44* (2006.01)

(52) U.S. Cl.
USPC ........................................ 623/17.16

(58) Field of Classification Search
USPC .............................. 623/17.11–17.16; 411/14
See application file for complete search history.

(56) References Cited

U.S. PATENT DOCUMENTS

| | | | |
|---|---|---|---|
| 4,463,753 A | 8/1984 | Gustilo |
| 4,599,086 A | 7/1986 | Doty |
| 4,743,256 A | 5/1988 | Brantigan |
| 4,790,303 A | 12/1988 | Steffee |
| 4,892,545 A | 1/1990 | Budde et al. |
| 4,904,261 A | 2/1990 | Davis et al. |
| 5,002,576 A | 3/1991 | Fritz et al. |
| 5,062,850 A | 11/1991 | Haid, Jr. et al. |
| 5,397,364 A | 3/1995 | Boyd et al. |
| 5,405,391 A | 4/1995 | Hednerson et al. |
| 5,534,031 A | 7/1996 | Matsuzaki et al. |
| 5,549,612 A | 8/1996 | Worrick, III et al. |
| 5,616,144 A | 4/1997 | Worrick, III et al. |
| 5,713,899 A | 2/1998 | Godard et al. |
| 5,843,082 A | 12/1998 | Benzel et al. |
| 5,861,041 A | 1/1999 | Tienboon |
| 5,876,456 A | 3/1999 | Bachmayer et al. |
| 5,876,457 A | 3/1999 | Goldstein et al. |
| 5,893,889 A | 4/1999 | Harrington |
| 5,951,558 A | 9/1999 | Fiz |
| 6,099,531 A | 8/2000 | Bonutti |
| 6,120,503 A | 9/2000 | Michelson |
| 6,123,705 A | 9/2000 | Michelson |
| 6,136,001 A | 10/2000 | Michelson |

(Continued)

FOREIGN PATENT DOCUMENTS

| | | | |
|---|---|---|---|
| CA | 2444232 A1 | 8/1998 |
| CA | 2523814 A1 | 8/1998 |

(Continued)

*Primary Examiner* — Mary Hoffman
(74) *Attorney, Agent, or Firm* — NuVasive, Inc.; Jonathan Spangler; Jennifer Russell

(57) ABSTRACT

A spinal fusion implant having a body dimensioned for use in the cervical spine. The body has an anterior height that is greater than the posterior height and a fusion aperture defined by an anterior wall, posterior wall and first and second lateral walls. The anterior wall includes a plurality of fastener apertures extending therethrough at oblique angles relative to the horizontal axis. The plurality of fastener apertures have an anterior diameter that is greater than the posterior diameter and include an annular groove dimensioned to retain the head of a bone fastener therein.

14 Claims, 22 Drawing Sheets

(56) References Cited

U.S. PATENT DOCUMENTS

| | | |
|---|---|---|
| 6,139,550 A | 10/2000 | Michelson |
| 6,152,927 A | 11/2000 | Farris et al. |
| 6,193,721 B1 | 2/2001 | Michelson |
| 6,214,005 B1 | 4/2001 | Benzel et al. |
| 6,235,059 B1 | 5/2001 | Benezech |
| 6,258,089 B1 | 7/2001 | Campbell et al. |
| 6,306,139 B1 | 10/2001 | Fuentes |
| 6,306,170 B2 | 10/2001 | Ray |
| 6,364,880 B1 | 4/2002 | Michelson |
| 6,371,986 B1 | 4/2002 | Bagby |
| 6,395,030 B1 | 5/2002 | Songer et al. |
| 6,423,063 B1 | 7/2002 | Bonutti |
| 6,468,311 B2 | 10/2002 | Boyd et al. |
| 6,471,724 B2 | 10/2002 | Zdeblick et al. |
| 6,485,517 B1 | 11/2002 | Michelson |
| 6,540,785 B1 | 4/2003 | Gill et al. |
| 6,558,423 B1 | 5/2003 | Michelson |
| 6,558,424 B2 | 5/2003 | Thalgott |
| 6,562,073 B2 | 5/2003 | Foley |
| 6,576,017 B2 | 6/2003 | Foley et al. |
| 6,579,290 B1 | 6/2003 | Hardcastle et al. |
| 6,626,907 B2 | 9/2003 | Campbell et al. |
| 6,652,525 B1 | 11/2003 | Assaker et al. |
| 6,669,700 B1 | 12/2003 | Farris et al. |
| 6,682,561 B2 | 1/2004 | Songer et al. |
| 6,730,127 B2 | 5/2004 | Michelson |
| 6,911,045 B2 | 6/2005 | Shimp |
| 6,916,320 B2 | 7/2005 | Michelson |
| 6,926,718 B1 | 8/2005 | Michelson |
| 6,969,390 B2 | 11/2005 | Michelson |
| 6,972,019 B2 | 12/2005 | Michelson |
| 7,001,385 B2 * | 2/2006 | Bonutti ............ 606/60 |
| 7,001,387 B2 | 2/2006 | Farris et al. |
| 7,033,394 B2 | 4/2006 | Michelson |
| 7,041,135 B2 | 5/2006 | Michelson |
| 7,063,701 B2 | 6/2006 | Michelson |
| 7,077,844 B2 | 7/2006 | Michelson |
| 7,094,239 B1 | 8/2006 | Michelson |
| 7,112,222 B2 | 9/2006 | Fraser et al. |
| 7,137,984 B2 | 11/2006 | Michelson |
| 7,163,561 B2 | 1/2007 | Michelson |
| 7,172,627 B2 | 2/2007 | Fiere et al. |
| 7,226,482 B2 | 6/2007 | Messerli et al. |
| 7,232,464 B2 | 6/2007 | Mathieu et al. |
| 7,235,105 B2 | 6/2007 | Jackson |
| 7,255,698 B2 | 8/2007 | Michelson |
| 7,267,690 B2 | 9/2007 | Felt |
| 7,323,011 B2 | 1/2008 | Shepard et al. |
| 7,491,237 B2 | 2/2009 | Randall et al. |
| 7,621,956 B2 | 11/2009 | Paul et al. |
| 7,621,960 B2 | 11/2009 | Boyd et al. |
| 7,637,951 B2 | 12/2009 | Michelson |
| 7,637,954 B2 | 12/2009 | Michelson |
| 7,651,497 B2 | 1/2010 | Michelson |
| 7,662,185 B2 | 2/2010 | Alfaro et al. |
| 7,776,093 B2 | 8/2010 | Wolek et al. |
| D623,750 S | 9/2010 | Duffield et al. |
| 7,846,207 B2 | 12/2010 | Lechmann et al. |
| 7,914,554 B2 | 3/2011 | Michelson |
| 8,048,075 B2 | 11/2011 | Michelson |
| 2005/0177245 A1 | 8/2005 | Leatherbury et al. |
| 2005/0187552 A1 | 8/2005 | Michelson |
| 2005/0283152 A1 * | 12/2005 | Lindemann et al. ............ 606/61 |
| 2006/0079961 A1 | 4/2006 | Michelson |
| 2006/0085071 A1 | 4/2006 | Lechman et al. |
| 2006/0122703 A1 | 6/2006 | Aebi et al. |
| 2006/0200166 A1 | 9/2006 | Hanson et al. |
| 2006/0206208 A1 | 9/2006 | Michelson |
| 2006/0282165 A1 | 12/2006 | Pisharodi |
| 2007/0233253 A1 | 10/2007 | Bray et al. |
| 2007/0270965 A1 | 11/2007 | Ferguson |
| 2008/0082173 A1 | 4/2008 | Delurio et al. |
| 2008/0177307 A1 | 7/2008 | Moskowitz et al. |
| 2008/0249569 A1 | 10/2008 | Waugh et al. |
| 2008/0249575 A1 * | 10/2008 | Waugh et al. ................. 606/305 |
| 2008/0281425 A1 | 11/2008 | Thalgott et al. |
| 2008/0306596 A1 | 12/2008 | Jones et al. |
| 2008/0312742 A1 | 12/2008 | Abernathie |
| 2009/0088849 A1 | 4/2009 | Armstrong et al. |
| 2009/0099659 A1 | 4/2009 | Oh et al. |
| 2009/0105831 A1 | 4/2009 | Jones et al. |
| 2009/0157186 A1 | 6/2009 | Magerl |
| 2009/0182430 A1 | 7/2009 | Tyber et al. |
| 2009/0210062 A1 | 8/2009 | Thalgott et al. |
| 2009/0210063 A1 | 8/2009 | Barrett |
| 2009/0224023 A1 | 9/2009 | Moskowitz et al. |
| 2009/0234455 A1 | 9/2009 | Moskowitz et al. |
| 2009/0259256 A1 | 10/2009 | Miller |
| 2009/0270991 A1 | 10/2009 | Michelson |
| 2010/0049324 A1 | 2/2010 | Valdevit et al. |
| 2010/0057206 A1 | 3/2010 | Duffield et al. |
| 2010/0125334 A1 | 5/2010 | Krueger |
| 2010/0145460 A1 | 6/2010 | McDonough et al. |
| 2010/0185288 A1 | 7/2010 | Carls et al. |
| 2010/0204739 A1 | 8/2010 | Bae et al. |
| 2010/0249935 A1 | 9/2010 | Slivka et al. |

FOREIGN PATENT DOCUMENTS

| | | |
|---|---|---|
| CA | 2533713 A1 | 8/1998 |
| DE | 29511146 U1 | 1/1996 |
| DE | 19630256 A1 | 1/1998 |
| EP | 0179695 A1 | 4/1986 |
| EP | 0560140 A1 | 9/1993 |
| FR | 2727003 A1 | 5/1996 |
| FR | 2727619 A1 | 6/1996 |
| FR | 2923155 A1 | 5/2009 |
| JP | 4114644 A | 4/1992 |
| SU | 1519677 A1 | 11/1989 |
| SU | 1715338 A1 | 2/1992 |
| WO | WO-9525474 A1 | 9/1995 |
| WO | WO-9720526 A1 | 6/1997 |
| WO | WO-9723175 A1 | 7/1997 |
| WO | WO-9963913 A2 | 12/1999 |
| WO | WO-9963914 A1 | 12/1999 |
| WO | WO-02065957 A2 | 8/2002 |
| WO | WO-2007098288 A2 | 8/2007 |
| WO | WO-2009064644 A1 | 5/2009 |
| WO | WO-2009071153 A1 | 6/2009 |
| WO | WO-2009091775 A2 | 7/2009 |
| WO | WO-2009092961 A2 | 7/2009 |
| WO | WO-2009099559 A2 | 8/2009 |
| WO | WO-2009144671 A1 | 12/2009 |
| WO | WO-2010028045 A1 | 3/2010 |
| WO | WO-2010028095 A1 | 3/2010 |
| WO | WO-2010079993 A2 | 7/2010 |

* cited by examiner

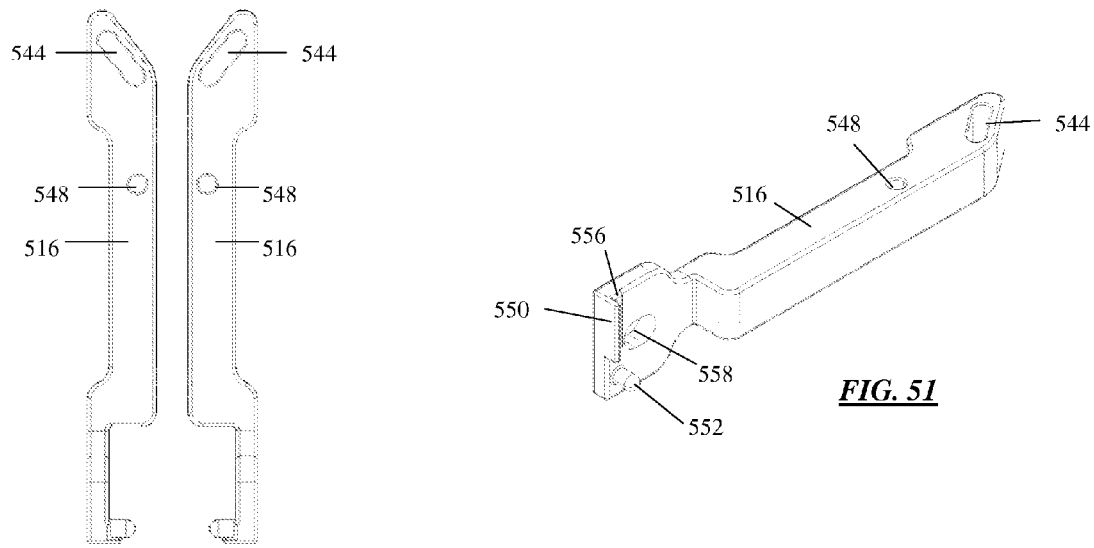
FIG. 50
FIG. 51
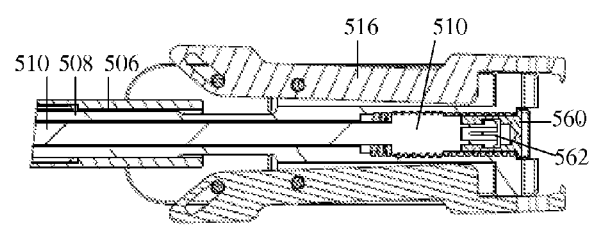
FIG. 52
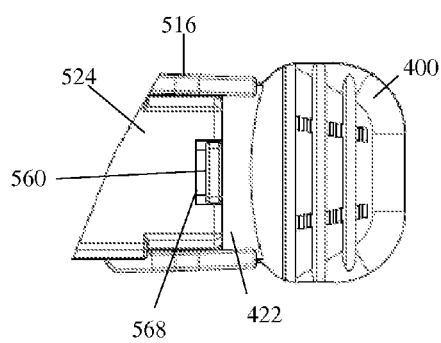
FIG. 53A
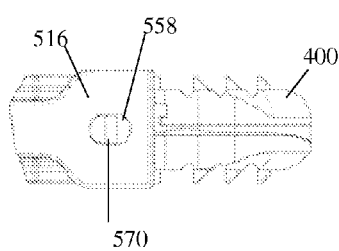
FIG. 53B

SPINAL IMPLANTS, INSTRUMENTS AND RELATED METHODS

CROSS-REFERENCE TO RELATED APPLICATIONS

This application is a non-provisional patent application claiming the benefit of priority from U.S. Provisional Patent Application Ser. No. 61/260,396, filed on Nov. 11, 2009, U.S. Provisional Application Patent Application Ser. No. 61/328, 115 filed on Apr. 26, 2010, and U.S. Provisional Patent Application Ser. No. 61/389,956, filed on Oct. 5, 2010, the entire contents of which are hereby expressly incorporated by reference into this disclosure as if set forth in its entirety herein.

FIELD

The present invention relates generally to spinal surgery and to implants, instruments and methods for performing spinal fusion and total disc replacement procedures.

BACKGROUND

Many millions of people suffer from back pain every year in across the globe. One of the prominent causes of back pain and related disabilities is the rupture or degeneration of one or more intervertebral discs in the spine due to trauma, disease, and/or aging. Displaced, damaged, or degenerated discs can result in irritation or damage to the delicate nerve tissues in close proximity to the spine. Surgical procedures are commonly performed to correct conditions and pain associated with displaced, damaged, or degenerated intervertebral discs. Generally, spinal fusion procedures involve removing some or the all of the diseased or damaged disc, and inserting one or more intervertebral implants into the resulting void in the disc space to restore the appropriate spacing between the vertebral bodies bordering the disc space. In the cervical spine, anterior cervical discectomy and fusion (ACDF) procedures provide unparalleled access to a desired cervical spinal target site. The ACDF technique involves approaching the cervical spine through the neck and exposing the front of the cervical spine, as opposed to the back. Approaching the cervical spine this way generally allows for greater exposure and a more complete excision of the damaged disc. Introducing the intervertebral implant serves to restore the height between adjacent vertebrae ("disc height"), which reduces, if not eliminates, neural impingement associated with a damaged or diseased disc.

In recent years, the area of total disc replacement has experienced proliferated growth and attention from the medical community. Known total disc replacement devices generally require some form of articulation or inherent flexibility in the device to permit a spine having the device to maintain its natural posture and range of motion as much as possible. Such devices typically include between 2 and 4 separate components constructed from any number of materials. Generally speaking, these components include a pair of cover plates for engagement with opposed vertebral body endplates and one or more internal components for simulating the intervertebral disc. These multi-part total disc replacement devices provide good results, however the surgical technique for implantation can be challenging. The best results are achieved when the multi-part total disc replacement device is properly positioned in the intervertebral disc space, making the need for specialized insertion instruments an important area of focus.

The present invention is directed at overcoming, or at least reducing the effects of, one or more of the problems set forth above.

SUMMARY

In a preferred aspect, the spinal fusion implant includes a body configured for implantation between a superior and an inferior vertebra, having a top surface and a bottom surface, an anterior height and a posterior height, and a fusion aperture defined by an anterior wall, a posterior wall, and first and second lateral walls. The body may be constructed of radiolucent, non-bone material. The top and/or bottom surfaces of the body may further include anti-migration features. The body may also include at least one radiopaque marker. In some implementations, the body includes an engagement groove in the lateral walls dimensioned to receive the gripping elements of an inserter instrument.

The spinal implant further includes a plurality of fastener apertures extending through the anterior wall at oblique angles relative to a horizontal axis. Each of the fastener apertures is dimensioned to receive a bone fastener for insertion into one of the superior or inferior vertebrae. The bone fastener has a head, a shank and a collar disposed between the head and shank.

The plurality of fastener apertures have an anterior diameter and a posterior diameter, wherein the anterior diameter is greater than the posterior diameter. The fastener apertures also comprise an annular groove dimensioned to retain the head of the bone fastener therein. In a preferred embodiment, the fastener apertures comprise a visualization marker proximal to the annular groove. In some implementations, the spinal fusion implant may further comprise a washer disposed within the annular groove of the fastener apertures. In a preferred embodiment, the washer includes at least one surface that has friction surface features.

In one aspect, the fastener apertures extend through the anterior wall at oblique angles relative to the horizontal axis are between 25° and 50°. Preferably, the oblique angle is 40°.

In another aspect, the plurality of fastener apertures extend through the anterior wall at angles oblique to a longitudinal axis. The oblique angles relative to the longitudinal axis may be between 5° and 15°.

In a preferred embodiment, the plurality of fastener apertures is equal to three. At least two of the fastener apertures may be dimensioned to receive the bone fastener for insertion into the inferior vertebra.

In one aspect, the instrument for inserting a spinal implant comprises an elongated tubular element having a distal end and a proximal end, the distal end configured with a fixed inserter body and the proximal end configured with thumbwheel housing having at least one thumbwheel; an inner shaft configured for placement within the elongated tubular element having a distal end and a proximal end, the distal end configured with an actuating member that is actuated by the at least one thumbwheel; and a pair of grasper arms that are each configured with a guide slot and a pivot pin aperture, wherein the guide slots are translationally mounted to the fixed inserter body with a pair of guide posts, and wherein the pivot pin apertures are pivotably mounted to the actuating member with a pair of pivot pins; wherein rotation of the at least one thumbwheel displaces the inserter shaft causing the guide slots to translate about the first pair of guide posts thereby moving the grasper arms to releasably engage the spinal implant.

In another aspect, the elongated tubular element further comprises a handle disposed on the proximal end of the thumbwheel housing.

In some implementations, the gripping arms are configured with engagement prongs that engage with the spinal implant. The engagement prongs may be configured with different engagement geometries. For example, the different engagement geometries may be configured as an elongated prong and a circular prong. The gripping arms may be configured with a shoulder to preferentially matingly engage the elongated prong first into position within the spinal implant.

In one embodiment, the gripping arms are configured with a visualization aperture that allows X-ray imaging of the position of the spinal implant relative to the insertion instrument.

In another embodiment, the actuating member is configured with a central protrusion and the fixed insert base is configured with a central slot, wherein the central protrusion and central slot matingly engage to resist misalignment of the actuating member during actuation.

In some implementations, the instrument further comprises an inner rod configured for placement within the inner shaft having a distal end and a proximal end, wherein the distal end is configured for securing an attachment and the proximal end is configured to engage with a second thumbwheel. The inner rod may be configured for attachment of a screw guide attachment. In one embodiment, the screw guide attachment is configured with screw guide holes sized and dimensioned for insertion of screws into the spinal implant. In another aspect, the inner rod may be configured for attachment of a distal pusher tip that applies pressure to the spinal implant.

In yet another embodiment, the thumbwheel housing is configured with a side portion that narrows to allow more surface area for rotation of the at least one thumbwheel.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 50 shows the gripping arms in the closed position;

FIG. 51 is a perspective view of one of the gripping arms;

FIG. 52 is a sectional, detailed view of the distal insertion head of the insertion instrument of FIG. 47;

FIG. 53A is a detailed top view and FIG. 53B is a detailed side view of the distal insertion head with the multi-part implant;

DESCRIPTION OF THE PREFERRED EMBODIMENT

Figure 1:
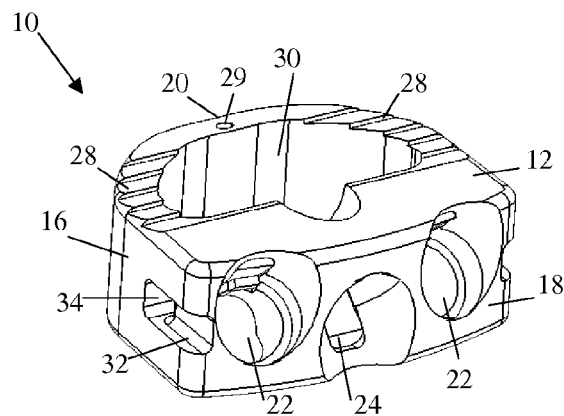
FIG. 1 is a perspective view of a spinal implant, according to one example embodiment.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant disclosed herein boasts a variety of inventive features and components that warrant patent protection, both individually and in combination.

FIGS. 1-4 illustrate a spinal fusion implant 10 according to a first broad aspect of the present invention. The spinal fusion implant 10 may be constructed of any suitable non-bone composition having suitable radiolucent characteristics, including but not limited to, polymer compositions (e.g. poly-ether-ether-ketone (PEEK), poly-ether-ketone-ketone (PEKK), or carbon-fiber reinforced PEEK (CFRP)) or any combination thereof. The spinal fusion implant 10 includes a top surface 12, a bottom surface 14, two lateral sides 16, an anterior side 18, and a posterior side 20 (each defined relative to the regions of the target disc space when implanted). According to a preferred method of implantation the spinal fusion implant may be implanted from an anterior approach such that anterior side 18 is the trailing side and posterior side 20 is the leading side during insertion. The anterior side 18 includes a pair of upper screw holes 22 and a lower screw hole 24 flanked by upper screw holes 22 for receiving bone screws 26 therethrough.

Once deposited in the intervertebral disc space, the spinal implant 10 effects spinal fusion over time as the natural healing process integrates and binds the implant 10 within the intervertebral space by allowing a bony bridge to form through the implant 10 and between the adjacent vertebral bodies. Top surface 12 and opposed bottom surface 14 are adapted for contact with the upper and lower vertebra adjacent the disc space, respectively. Bone screws 26 may be introduced through the screw holes 22, 24 and into the adjacent vertebral bodies to fix the implant 10 in the desired position within the disc space.

The top and bottom surfaces 12, 14 preferably include anti-migration features situated along at least a portion of their area. Anti-migration features are designed to increase the friction between the spinal fusion implant 10 and the adjacent contacting surfaces of the vertebral bodies so as to further prohibit migration of the spinal fusion implant 10 after placement and during the propagation of natural bony fusion. Such anti-migration features may include ridges (or teeth) 28 provided along at least a portion of the top surface 12 and/or bottom surface 14.

According to a preferred embodiment, the spinal fusion implant 10 includes at least one pin element 29 as a radiopaque marker. In one embodiment, the implant 10 includes one or more pin elements 29 disposed within the posterior side 20 of the implant 10. The pin element 29 may be manufactured from any of a variety of suitable radiopaque materials, including but not limited to a metal. The one or more pin elements 29 may each comprise a unitary element extending through the top surface 12 and bottom surface 14. Alternatively, each pin element 29 may comprise a shorter element which only extends through a single surface. Alternatively, each pin element 9 may comprise a shorter element that does not extend beyond either surface.

According to an additional embodiment, the top and bottom surfaces 12, 14, may be angled between the anterior side 18 and posterior side 20. In lumbar and cervical applications, the posterior side 20 will preferably be shorter in height than the anterior side 18 such that the implant tapers down from anterior side 18 to posterior side 20. In this manner, the implant 10 helps maintain the adjacent vertebral bodies in lordosis, which is the natural curvature found in the lumbar and cervical areas of the spine. The top and bottom surfaces 12, 14 may be configured in any number of suitable shapes to better match the natural contours of the vertebral end plates, such as, for example, concave, convex, or a combination of concave and convex.

Figure 2:
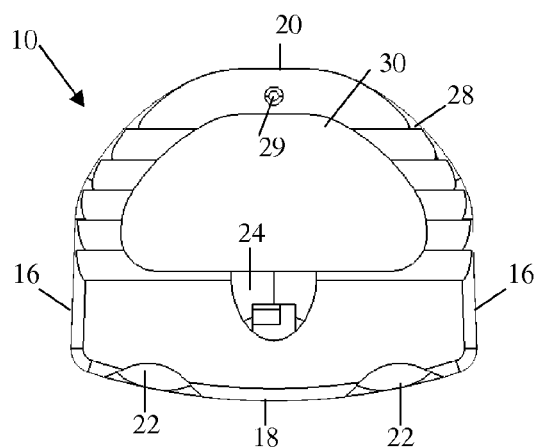
FIG. 2 is a top view of the spinal implant of FIG. 1.

As best viewed in FIG. 2, the implant includes a central cavity 30 extending through the top and bottom surfaces 12, 14. The generally D-shaped area of the cavity 30 is provided to maximize the size of the cavity to allow the greatest area for boney through growth, however, cavity 30 may be provided in any number of other suitable shapes, including but not limited to generally circular, oblong, and rectangular. Additionally, multiple cavities may be provided and separated by one or more support walls.

Fusion may be facilitated or augmented by introducing or positioning various osteoinductive materials within cavity 30 and/or adjacent to the spinal fusion implant 10. Such osteoinductive materials may be introduced before, during, or after insertion of the exemplary spinal fusion implant 10, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including not limited to any of a variety of poly (D, L-lactide-co-glycolide) based polymers.

Figure 3:
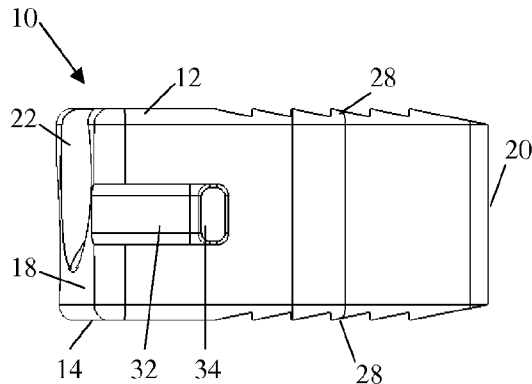
FIG. 3 is a side view of the spinal implant of FIG. 1.

FIG. 3 illustrates a lateral side 16 according to a one example embodiment. Lateral sides 16 each include an engagement groove 32 opening in anterior side 18 and extending distally to a point short of posterior side 20. At the distal most portion of the engagement grooves 32 the groove extends deeper into the lateral side wall 16 forming a gripping indent 34. As described below, engagement grooves 32 are configured to mate with an insertion instrument for positioning the implant 10 in the intervertebral disc space.

Figure 4:
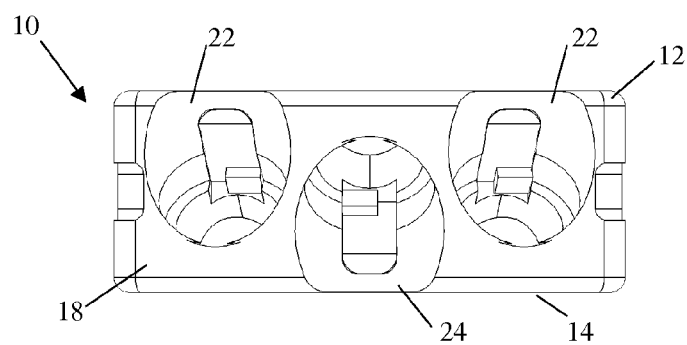
FIG. 4 is a front view of the spinal implant of FIG. 1.

As best appreciated in FIGS. 1 and 4, the outer screw holes 22 pass through the anterior side 18 at an angle such that when the screws 26 are inserted into the outer screw holes 22 they extend from the implant at an angle and penetrate into the vertebral body below the implant. By way of example, the upper screw holes 22 may be angled such that the screws penetrate into the vertebral body at an angle between 25 and 50 degrees, and preferably 40 degrees. Lower screw hole 24 also passes through the anterior side 18 at an angle but in the opposite direction as upper screw holes 22. Thus when the screw 26 is inserted into the lower screw hole 24 it extends from the implant at an angle and penetrates into the vertebral body above the implant. By way of example, the lower screw hole 24 may be angled such that the center screw penetrates into the vertebral body at an angle between 25 and 50 degrees, and preferably, 40 degrees. The upper screw holes 22 may also be angled such that the distal end of the screws 26 converge towards each other. By way of example, the screw holes 22 may be oriented such that the screws are angled medially between 5 and 15 degrees, and preferably 10 degrees. Though lower screw hole is shown adjacent bottom surface 14 and angled up towards the upper adjacent vertebra and the upper screw holes 22 are shown adjacent the top surface 12 and angled towards the lower adjacent vertebra, it will be appreciated that the implant 10 could be flipped such that the converse is true without deviating from the scope of the invention.

Figure 8:
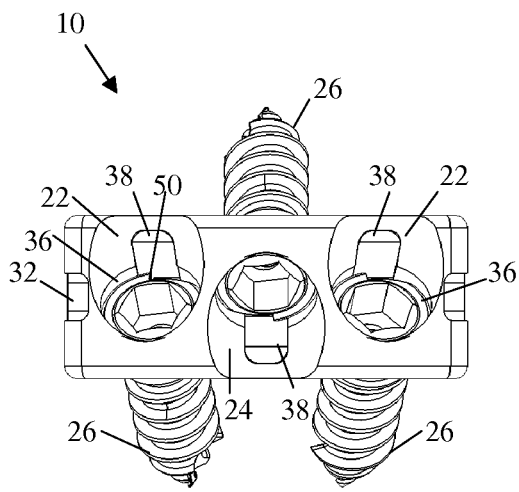
FIG. 8 is a front view of the spinal implant assembly including the spinal implant of FIG. 1 and four of the bone screws of FIG. 5.
Figure 9:
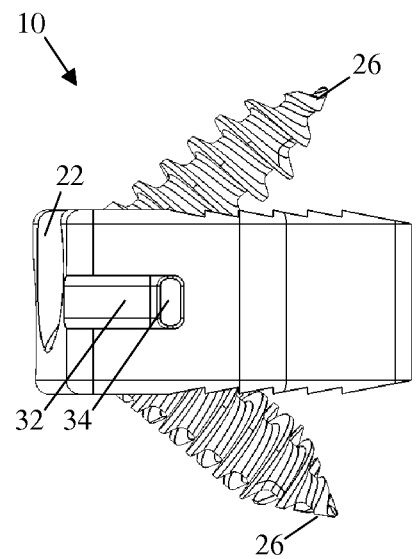
FIG. 9 is a side view of the spinal implant assembly of FIG. 8.
Figure 10:
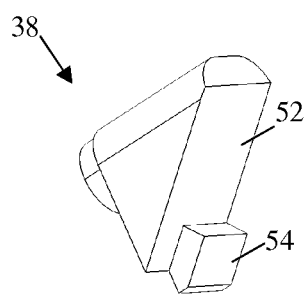
FIG. 10 is a perspective view of the stop tab within the screw holes in the spinal implant of FIG. 1
Figure 11:
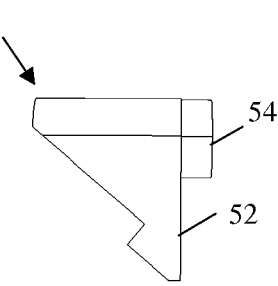
FIG. 11 is a side view of the stop tab of FIG. 10.
Figure 12:
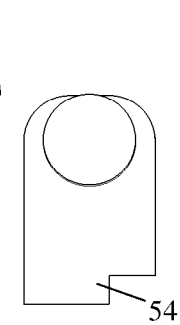
FIG. 12 is a top view of the stop tab of FIG. 10.
Figure 13:
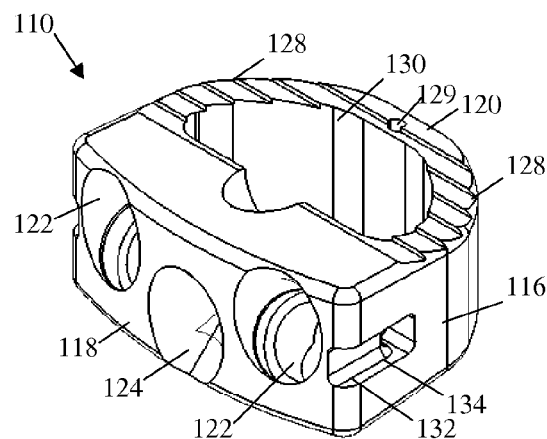
FIG. 13 is a perspective view of a spinal implant, according to a second embodiment.

With reference to FIG. 8, screw holes 22 and 24 are all equipped with an annular groove 36 formed about an interior surface of the screw hole. As will be described below, the annular groove 36 cooperates with the screw 26 when fully inserted in the hole to prevent the screw 26 from backing out of the screw hole. Also within each screw hole 22 and 24 is a stop tab 38. Stop tab 38 also cooperates with the screw 26 when fully inserted to provide a tactile indicator that the screw is fully inserted and thus retained by the annular groove 36.

Figure 5:
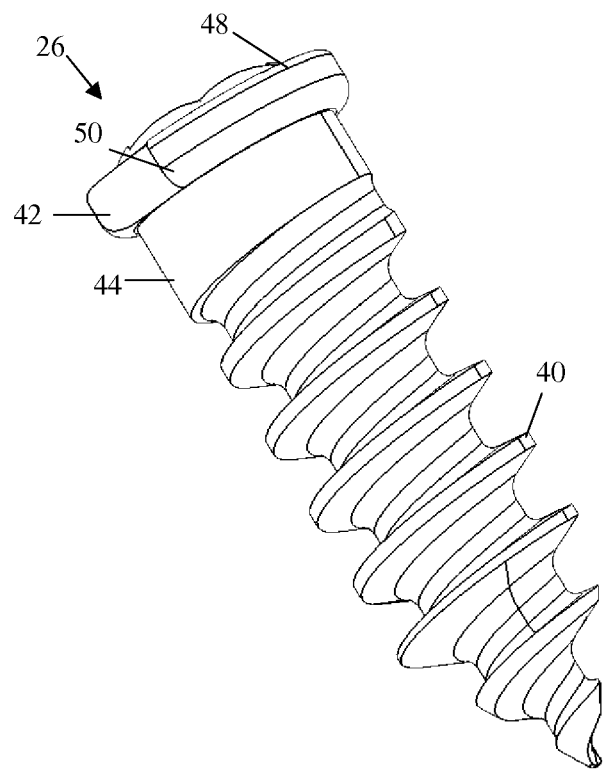
FIG. 5 is a perspective view of a bone screw, according to one example embodiment, for use with the spinal implant of FIG. 1.
Figure 6:
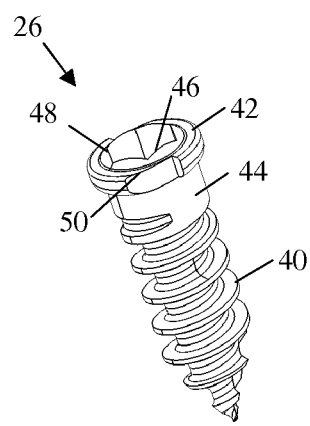
FIG. 6 is a second perspective view of the bone screw of FIG. 5.
Figure 7:
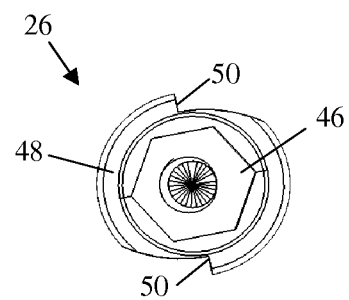
FIG. 7 is a top view of the bone screw of FIG. 5.

With reference to FIGS. 5-7 there is shown a bone screw 26 for use with the spinal fusion implant 10. The bone screw 26 has a threaded anchor shaft 40, a head 42, and a neck 44 separating the threaded shaft 40 and the head 42. The head further comprises a tooling recess 46, for example a hex recess, for engaging a driver and a rim 48. Rim 48 has a larger diameter than any other portion of the screw 26. Rim 48 includes two cut away regions forming two abutments 50 on the rim 48. The screw holes 22, 24 taper inward from a larger diameter at the anterior face of the implant to a smaller diameter adjacent the annular groove 36. The diameter of the rim 48 is slightly larger than the diameter of the interior of screw holes 22, 24 as it approaches the annular grove 36. As the screw is driven into the vertebra through screw hole 22 or 24 the rim 48 slightly deforms the area above the groove allowing the screw 26 to pass into the groove 36. The area above the annular groove 36 reforms capturing the head 42 in the groove 36 and preventing unwanted backout of the screw 26. As shown in FIGS. 9-12, stop tab 38 resides in a cavity formed adjacent to the interior of the screw hole 22, 24, such that the face 52 is the only portion of the stop tab 38 in communication with the interior of the screw hole. Except for stop block 54, the face 52 is generally flush with the interior wall of the screw hole and does not impede advancement of the screw 26 into the screw hole 22, 24. The stop block 54 extends into the hole. The stop block 54 is positioned low enough in the hole that it will not impede passage of the screw head 42 until the head is captured within annular groove 36. As pictured in FIG. 8, when the screw is fully seated, one of the abutments 50 will reach the stop block 54 and prevent further rotation of the screw 26. This indicates to the user that the screw 26 is fully captured in the annular groove 36.

FIGS. 13-26 illustrate a spinal fusion implant 110 according to a second broad aspect of the present invention. The spinal fusion implant 110 may be constructed of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. The spinal fusion implant 110 includes a top surface 112, a bottom surface 114, two lateral sides 116, an anterior side 118, and a posterior side 120 (each defined relative to the regions of the target disc space when implanted). According to a preferred method of implantation the spinal fusion implant may be implanted from an anterior approach such that anterior side 118 is the trailing side and posterior side 120 is the leading side during insertion. The anterior side 118 includes a pair of upper screw holes 122 and a lower screw hole 124 flanked by upper screw holes 122 for receiving bone screws 126 therethrough.

The spinal fusion implant 110 of the present invention may be used to provide temporary or permanent fixation along an orthopedic target site. Once deposited in the intervertebral disc space, the spinal implant 110 effects spinal fusion over time as the natural healing process integrates and binds the implant 110 within the intervertebral space by allowing a bony bridge to form through the implant 110 and between the adjacent vertebral bodies. Top surface 112 and opposed bottom surface 114 are both adapted for contact with the upper and lower vertebra adjacent the disc space. Bone screws 126 may be introduced through the screw holes 122, 124 and into the adjacent vertebral bodies to fix the implant 10 in the desired position within the disc space.

The top and bottom surfaces 112, 114 preferably include anti-migration features situated along at least a portion of their area. Anti-migration features are designed to increase the friction between the spinal fusion implant 110 and the adjacent contacting surfaces of the vertebral bodies so as to further prohibit migration of the spinal fusion implant 110 after placement and during the propagation of natural bony fusion. Such anti-migration features may include ridges (or teeth) 128 provided along at least a portion of the top surface 112 and/or bottom surface 114.

Figure 15:
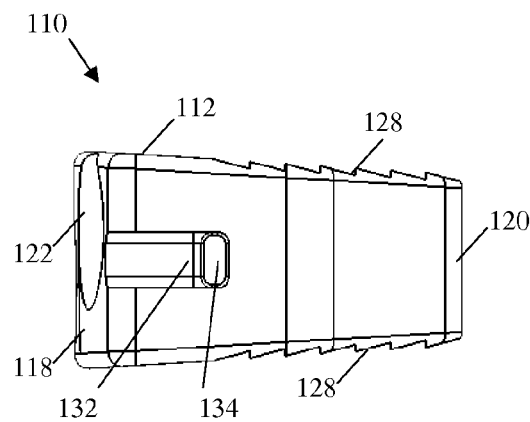
FIG. 15 is a side view of the spinal implant of FIG. 13.

The top and bottom surfaces 112, 114, may be angled between the anterior side 118 and posterior side 120, as illustrated in FIG. 15. In lumbar and cervical applications, the posterior side 120 will preferably be shorter in height than the anterior side 118 such that the implant tapers down from anterior side 118 to posterior side 120. In this manner, the implant 110 helps maintain the adjacent vertebral bodies in lordosis, which is the natural curvature found in the lumbar and cervical areas of the spine. The top and bottom surfaces 112, 114 may be configured in any number of suitable shapes to better match the natural contours of the vertebral end plates, such as, for example, concave, convex, or a combination of concave and convex.

Figure 14:
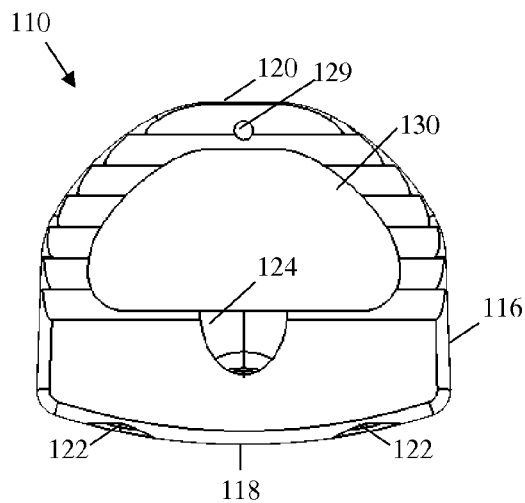
FIG. 14 is a top view of the spinal implant of FIG. 13.

As best viewed in FIG. 14, the implant includes a central cavity 130 extending through the top and bottom surfaces 112, 114. The generally D-shaped area of the cavity 130 is provided to maximize the size of the cavity to allow the greatest area for bony through growth, however, cavity 130 may be provided in any number of other suitable shapes, including but not limited to generally circular, oblong, and rectangular. Additionally, multiple cavities may be provided and separated by one or more support walls.

Fusion may be facilitated or augmented by introducing or positioning various osteoinductive materials within cavity 130 and/or adjacent to the spinal fusion implant 110. Such osteoinductive materials may be introduced before, during, or after insertion of the exemplary spinal fusion implant 110, and may include (but are not necessarily limited to) autologous bone harvested from the patient receiving the spinal fusion implant 110, bone allograft, bone xenograft, any number of non-bone implants (e.g. ceramic, metallic, polymer), bone morphogenic protein, and bio-resorbable compositions, including not limited to any of a variety of poly (D, L-lactide-co-glycolide) based polymers.

FIG. 15 illustrates a lateral side 116 according to a one example embodiment. Lateral sides 116 each include an engagement groove 132 opening in anterior side 118 and extending distally to a point short of posterior side 120. At the distal most portion of the engagement grooves 132 the groove extends deeper into the lateral side wall 116 forming a gripping indent 134. As described below, engagement grooves 132 are configured to mate with an insertion instrument for positioning the implant 110 in the intervertebral disc space As best appreciated in FIGS. 13 and 16, the outer screw holes 122 pass through the anterior side 118 at an angle such that when the screws 126 are inserted into the outer screw holes 122 they extend from the implant at an angle and penetrate into the vertebral body below the implant. By way of example, the upper screw holes 122 may be angled such that the screws penetrate into the vertebral body at an angle between 25 and 50 degrees, and preferably 40 degrees. Lower screw hole 124 also passes through the anterior side 118 at an angle but in the opposite direction as upper screw holes 122. Thus, when the screw 126 is inserted into the lower screw hole 124, it extends from the implant at an angle and penetrates into the vertebral body above the implant. By way of example, the lower screw hole 124 may be angled such that the center screw penetrates into the vertebral body at an angle between 25 and 50 degrees, and preferably, 40 degrees. The upper screw holes 122 may also be angled such that the distal end of the screws 126 converge towards each other. By way of example, the screw holes 122 may be oriented such that the screws are angled medially between 5 and 15 degrees, and preferably 10 degrees. Though the center, lower screw hole 124 is shown adjacent bottom surface 114 and angled up towards the upper adjacent vertebra and the outer screw holes 122 are shown adjacent the top surface 112 and angled towards the lower adjacent vertebra, it will be appreciated that the implant 110 could be flipped such that the converse is true without deviating from the scope of the invention.

The screw holes 122, 124 taper inward from a larger diameter at the anterior face of the implant to a smaller diameter adjacent the annular groove 136. The screw hole then widens into annular groove 136. The diameter of the annular groove 136 is slightly larger than the diameter of the screw head rim 152 while the diameter of the screw hole 122, 124 adjacent the annular groove 136 is smaller than the screw head rim 152. As the screw 126 is advanced through the implant, the screw head rim 152 deforms the softer implant material in the screw hole 122, 124 enough to travel past the smaller diameter entrance into the annular groove 136. Once inside the annular groove 136, the smaller diameter entrance prevents the screw 126 from backing out. A ledge 138 on the distal side of the annular groove 136 prevents the screw 126 from passing completely through the screw hole 122, 124.

Figure 16:
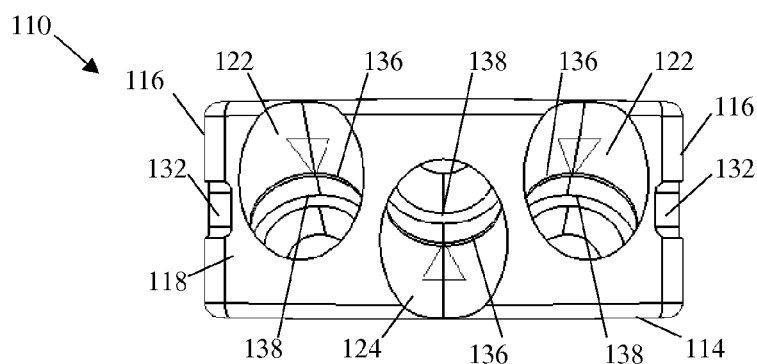
FIG. 16 is a front view of the spinal implant of FIG. 13.
Figure 19:
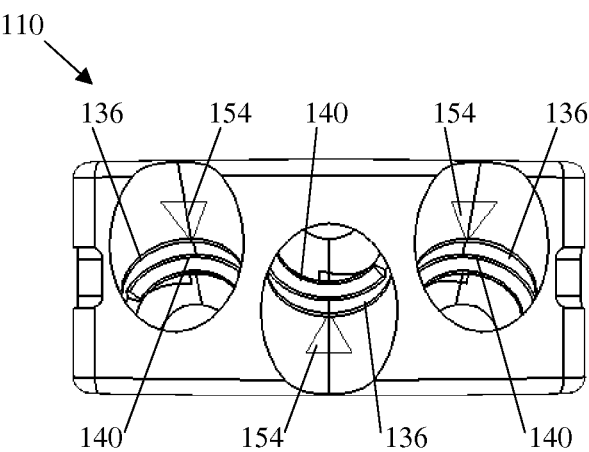
FIG. 19 is a front view of a spinal implant utilizing the keeled washer of FIG. 17.

As illustrated in FIGS. 16 and 19, the screw holes 122, 124 may also be provided with visible markers (e.g. arrows 154) proximal to the annular groove 136. Arrows 154 provide a visual indication that the screw 126 has been properly positioned beyond the annular groove 136. For example, the entire arrow is not visible (i.e. it is blocked from view by the screw head 146) until the screw 126 is fully seated within the annular groove 136. Furthermore, the ledge 138 (and/or washer 140 as described below) act as a stop for instruments including, but not limited to, the instruments described in FIGS. 54-58, 60, and 62. Particularly, the ledge 138 may act as a stop for the angled awl 320, angled driver 352, or the straight driver 356. The covers 344, 366, 368 initially fit within the screw holes 122, 124 but are restricted from further penetration at the ledge 138. The driving portions of the instruments 320, 352, 356 continue to travel and emerge from their respective cover 344, 366, 368 within the bone screw holes 122, 124.

Figure 17:
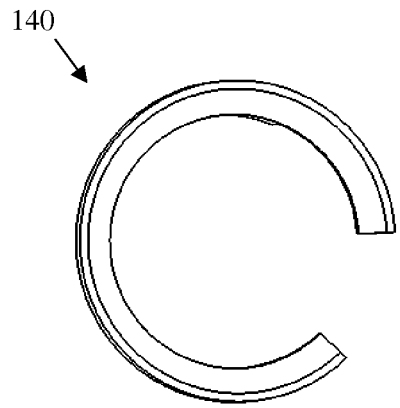
FIG. 17 is a front view of a keeled washer used in a third embodiment of the spinal implant assembly.
Figure 18:
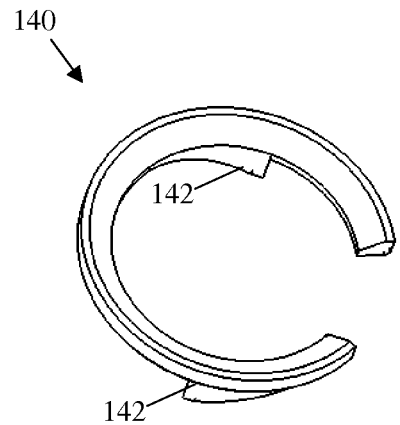
FIG. 18 is a perspective view of the keeled washer of FIG. 17.

With reference to FIGS. 17-19, according to one example embodiment, a washer 140 may be situated in the screw hole and positioned over the ledge 138. The washer 140 is preferably made of a harder material than the polymer composition of the implant, for example, including but not limited to titanium, or other surgical grade metals. According to the example shown in FIGS. 17-18, washer 140 may have a cut out region such that the washer is generally c-shaped for easier insertion into the screw hole during, or subsequent to, manufacturing. One or more keels 142 on the bottom of washer 140 hold it firmly in position within the implant. The washer 140 provides a hard contact surface for interfacing with the screws 126 and preventing excessive advancement or rotation of the screws. Surface friction features on the engagement surface of the washer 140, including, but not limited to, surface blasting may also provide tactile feedback to the surgeon when the screw head 146 fully interfaces with the washer 140, thereby confirming that the screw head 146 is fully advanced and captured in the annular groove 136 to prevent later backing out of the screw 126.

Figure 27:
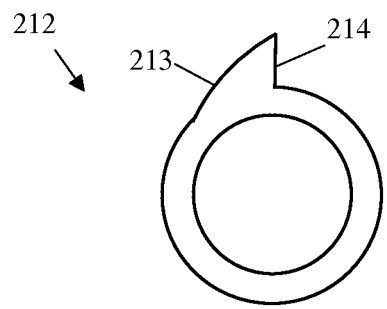
FIG. 27 is a front view of an abutment washer used in a spinal implant according to a fourth embodiment.
Figure 28:
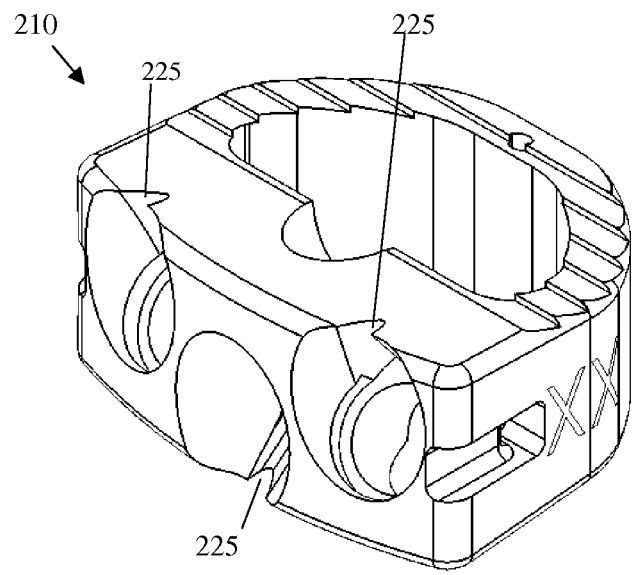
FIG. 28 is a perspective view of the spinal implant utilizing the abutment washer of FIG. 27.
Figure 29:
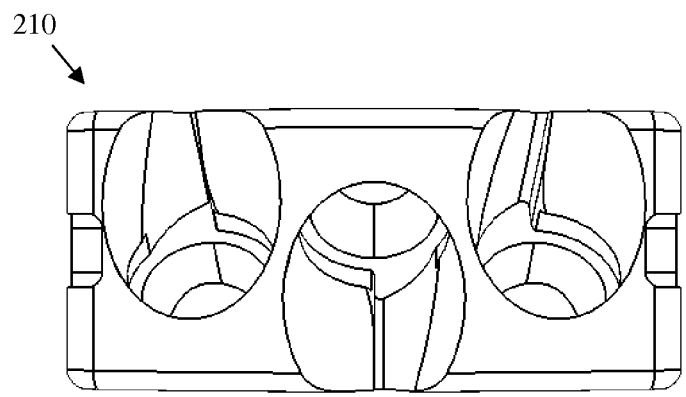
FIG. 29 is a front view of the spinal implant of FIG. 28.

FIGS. 27-29 illustrate an example embodiment of an implant 210. The implant 210 is substantially the same as the implant 110 except that a washer 212 takes the place of the washer 140. The washer 212 forms a complete circle and includes an extension 213 with an abutment face 214. The screw hole 222, 224 include a groove 225 complementary to the extension 213 such that the washer can slide into position in the annular groove adjacent the ledge. The abutment face 214 prevents the washer from rotating. Thus, when a screw head 146 is advanced into the annular groove as described above, the bottom of the screw head will interface with the top of the washer. Surface features on the engagement surface of the washer, the bottom of the screw head, or both will provide tactile feedback to the user as the screw head moves relative to the washer, confirming that the screw head is fully contained in the annular groove.

Figure 20:
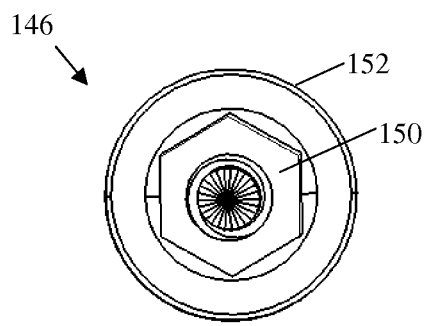
FIG. 20 is a top view of a bone screw, according to a second example embodiment, for use with the spinal implant of FIG. 13.
Figure 21:
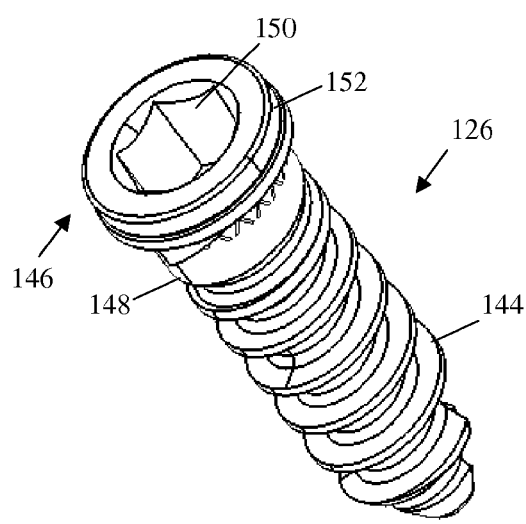
FIG. 21 is a perspective view of the bone screw of FIG. 20.
Figure 22:
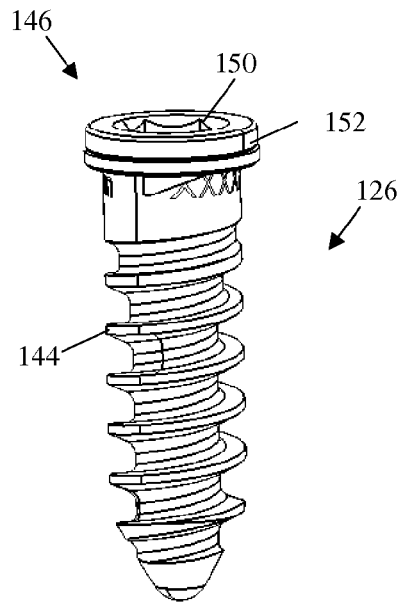
FIG. 22 is a front view of the bone screw of FIG. 20.
Figure 23:
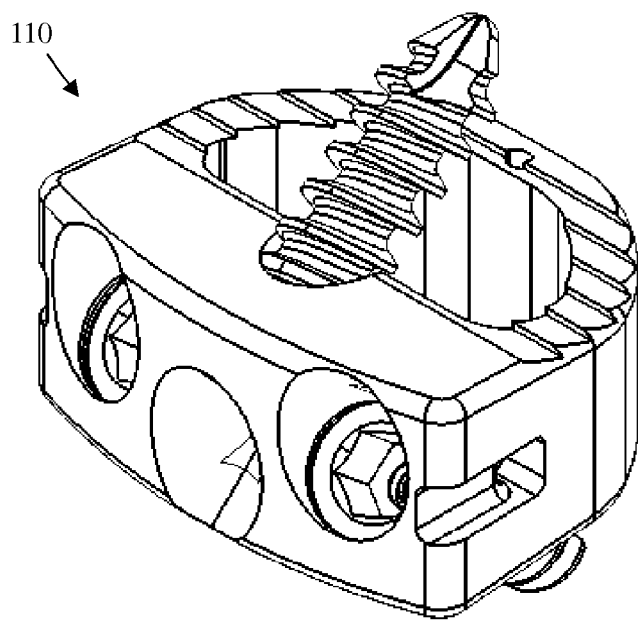
FIG. 23 is a perspective view of the spinal implant assembly including the spinal implant of FIG. 13 and four of the bone screws of FIG. 20.
Figure 24:
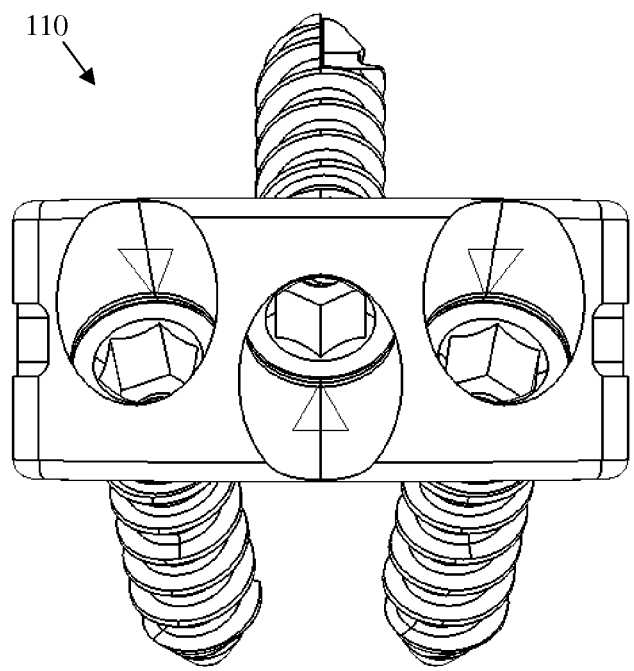
FIG. 24 is a front view of the spinal implant assembly of FIG. 23.
Figure 25:
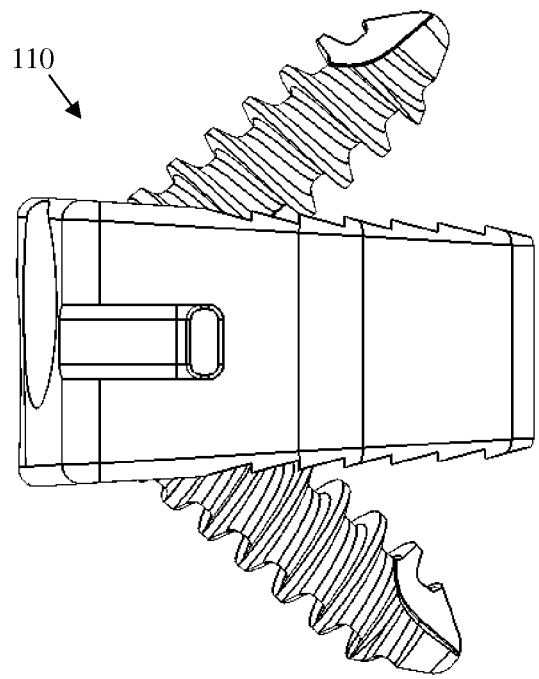
FIG. 25 is a side view of the spinal implant assembly of FIG. 23.
Figure 26:
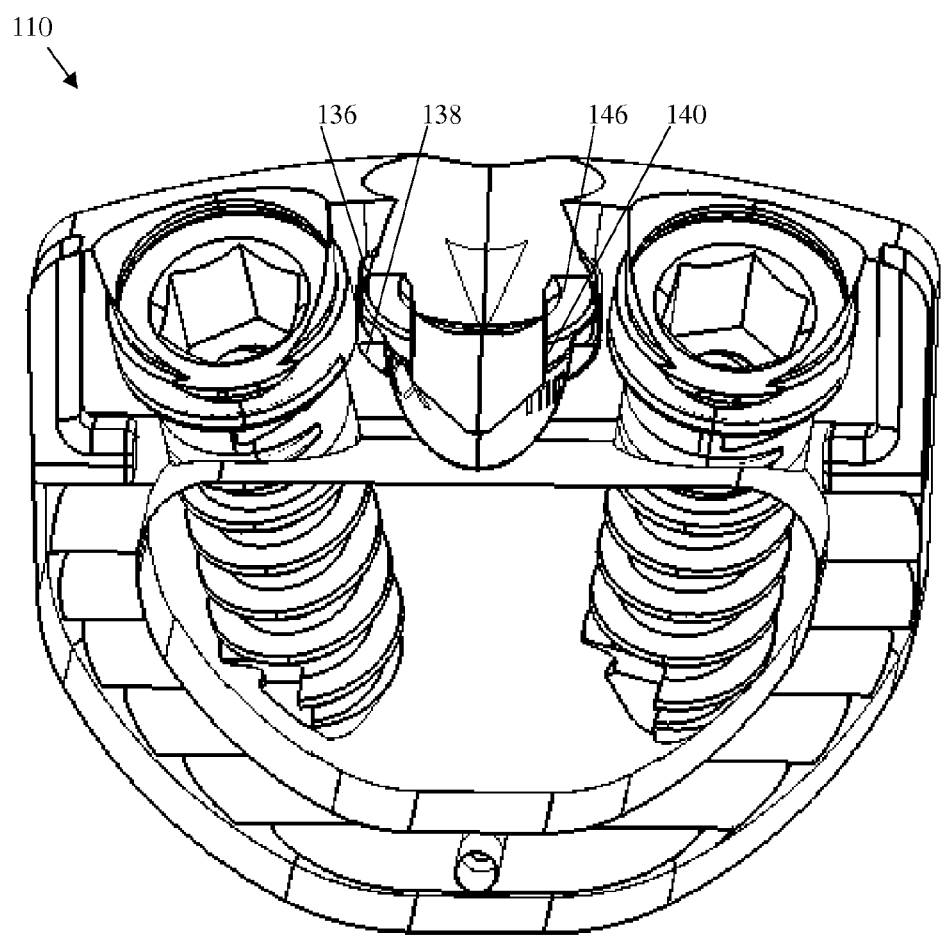
FIG. 26 is a partial-cross section view of the spinal implant assembly of FIG. 23 showing the interaction between the spinal implant of FIG. 13 and the bone screw of FIG. 20.

With reference to FIGS. 20-22, there is shown a bone screw 126 for use with the spinal fusion implant 110. The bone screw 126 has a threaded shaft 144, a head 146, and a neck 148 separating the threaded shaft 144 and the head 146. The head 146 further comprises a tooling recess 150, for example a hex recess, for engaging a driver (for example, the drivers 350, 352, 354, and 356 shown in FIGS. 59-62) and a rim 152. As the bone screw 126 is driven into the vertebra through the screw hole 122 or 124, the rim 152 slightly deforms the area above the annular groove 136 thereby allowing the bone screw 126 to pass into the annular groove 136. The area above the annular groove 136 at least partially reforms, capturing the head 146 thereby preventing unwanted backout of the bone screw 126. By way of example only, the diameter of the screw head 146 may be 4.445 mm while the diameter of the screw hole 122 or 124 at the narrowest point adjacent to the annular groove 136 may be 3.358 mm. Once in the annular groove, the screw engages the washer 140 and the surface-to-surface contact between the washer 140 and screw head 146 provide feedback to the user that the bone screw 126 is fully seated within the screw hole 122, 124. FIGS. 23-26 show perspective, anterior, lateral, and cross-sectional views of the spinal fusion implant 110 with the screws 126 fully positioned.

Figure 30:
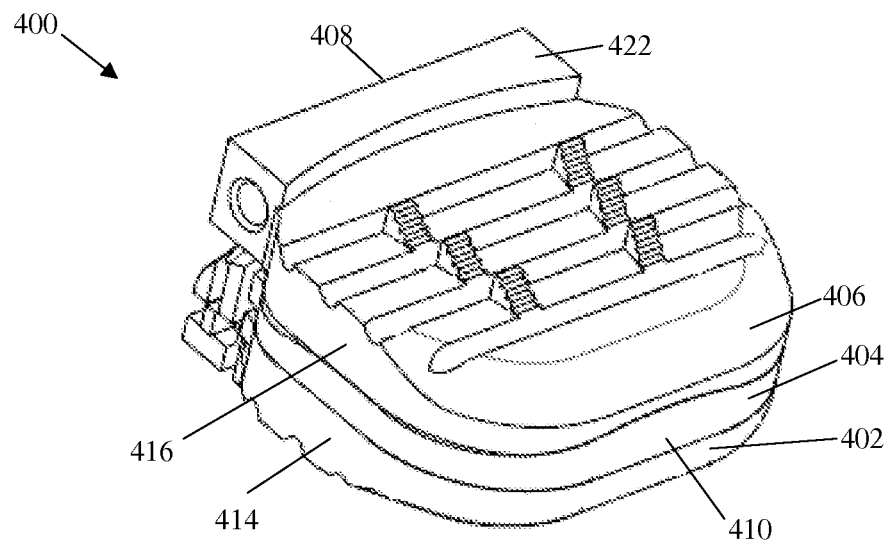
FIG. 30 is a perspective view of a multi-part spinal implant.
Figure 31:
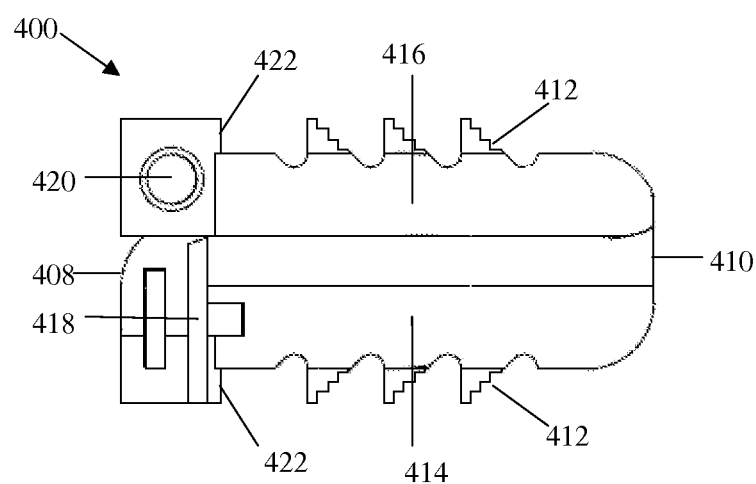
FIG. 31 is a side view of a multi-part spinal implant.

FIGS. 30-31 illustrate an example embodiment of a multi-part implant 400. The multi-part implant may be configured as described in U.S. Pat. No. 7,320,689, and U.S. Pat. No. 7,569,067, the disclosures of which are incorporated herein by reference. The multi-part implant includes a lower cover plate 402, an implant core 404, and an upper cover plate 406. The implant core 404 is made of a material with good sliding properties, for example, including but not limited to plastic or polyethylene. The lower cover plate 402 and upper cover plate 406 are made of a hard, resistant biocompatible material, in particular surgical grade metals, including but not limited to, titanium and cobalt chrome alloys. The implant core 404 is fixedly mounted to the lower cover plate 402 and the upper surface of the implant core 404 forms a spherical sliding surface. The implant core 404, together with the upper cover plate 406, correspond to form a spherical sliding surface that permits articulation of the multi-part implant 400. The implant core 404 has a large radius of articulation that mimics the arc-like translatory motion of the cervical spine.

According to a preferred method of implantation, the multi-part implant may be implanted from an anterior approach such that the anterior side 408 is the trailing side and posterior side 410 is the leading edge during insertion. Once deposited in the intervertebral disc space, the multi-part implant 400 preserves joint mobility by allowing motion between the fixed mounted implant core 404 on the lower cover plate 402 and upper cover plate 406. The outer surfaces 412 of the lower cover plate 402 and upper cover plate 406 are adapted for contact with the upper and lower vertebral adjacent the intervertebral disc space.

The outer surfaces 412 preferably include anti-migration features situated along at least a portion of their area. Anti-migration features are designed to increase the friction between the multi-part implant 400 and the adjacent contacting surface of the vertebral bodies so as to prevent migration of the multi-part implant after implantation and during propagation of the bony interface. Such anti-migration features may includes ridges, serrations, teeth, raised abutment surfaces and/or surface coatings provided along at least a portion of outer surfaces 412. The surface coatings may include, but are not limited to, titanium and calcium phosphate powders.

FIG. 31 illustrates a lateral side view of the multi-part implant 400. The lateral side 414 corresponds to the lower cover plate 402 and the lateral side 416 to the upper cover plate 406. Lateral sides 414 and 416 each include a recessed engagement structure near the anterior side 208 of the multi-part implant 400 which are configured to mate with an insertion instrument for positioning the multi-part implant 400 in the intervertebral disc space. Lateral sides 414, 416 of the lower cover plate 402 and upper cover plate 406, respectively, each include a recessed slot 418 and a recessed aperture 420 on opposite lateral sides of the raised abutment surface 422, for engagement with an insertion instrument.

Figure 32:
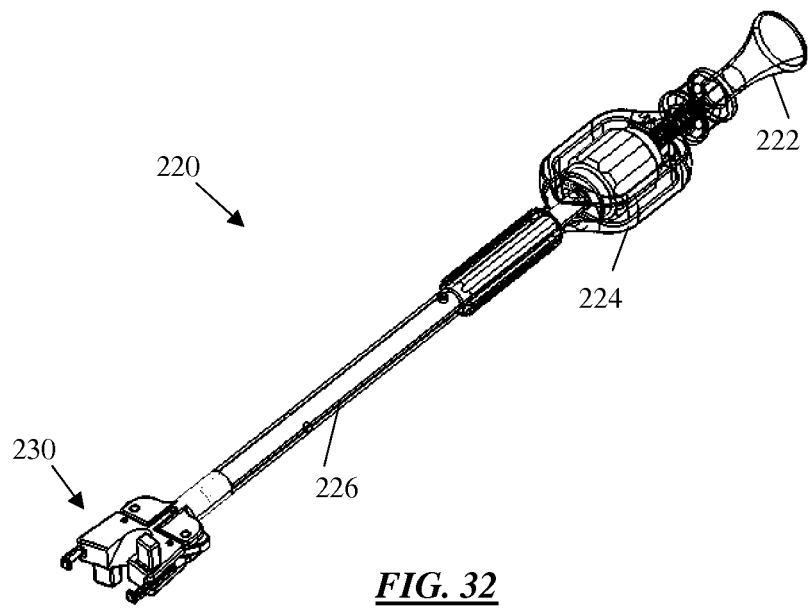
FIG. 32 is an insertion instrument according to a first embodiment.
Figure 33:
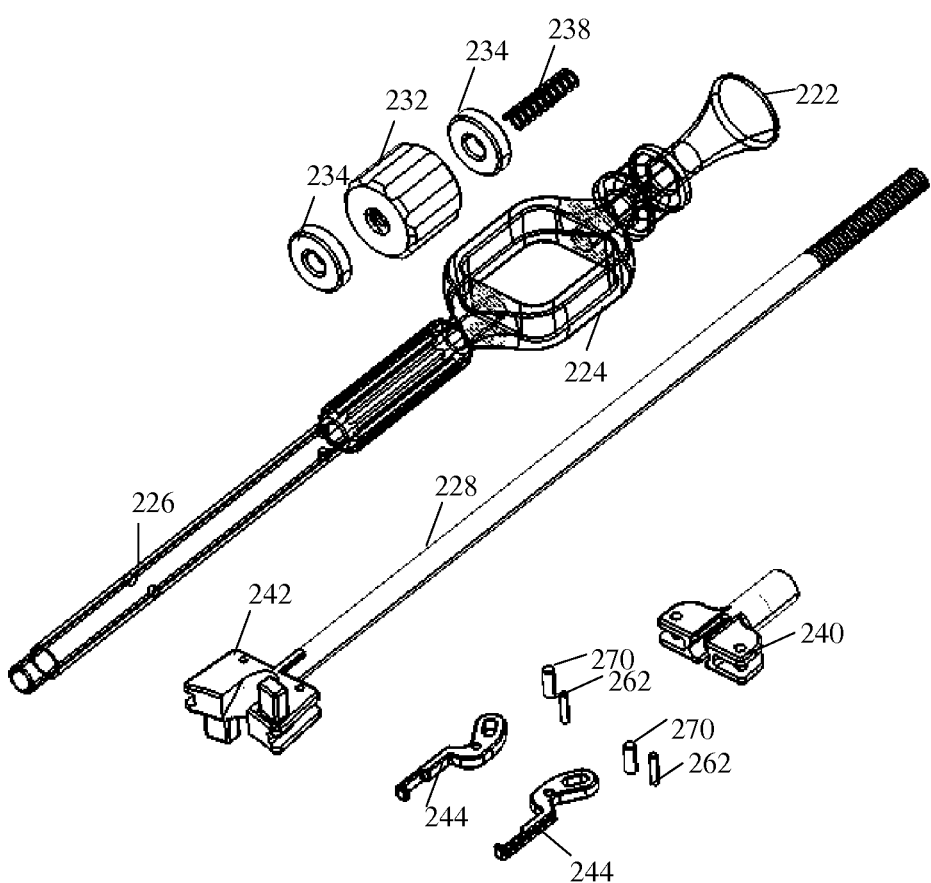
FIG. 33 is an exploded view of the insertion instrument of FIG. 32.

With reference to FIGS. 32-53, a number of inserters and other instruments which provide the user with a suite of choices for implanting the implant 10, 110, 210, 400 are described. According to a broad aspect, the insertion instruments include a handle 222, a thumbwheel housing 224, an elongate tubular element 226, an inserter shaft 228, and a distal inserter head 230, as illustrated in FIGS. 32-33.

The handle 222 is generally disposed at the proximal end of the insertion instrument 220. The handle 222 may be further equipped with a universal connector to allow the attachment of accessories for ease of handling of the insertion instrument (e.g. a straight handle or a T-handle, not shown). The handle 222 may be adapted to receive a striking force. FIGS. 32-38 detail an insertion instrument 220 according to a first embodiment of the present invention, preferably adapted for insertion from an anterior approach. The handle 222 is fixed to the thumbwheel housing 224 allowing easy handling by the user. By way of example, the thumbwheel housing 224 holds at least one thumbwheel 232, and at least one spacer 234. Because the handle 222 is fixed, the user has easy access to the thumbwheel 232 and can stably turn the thumbwheel 232 relative to the thumbwheel housing 224. Additionally, the relative orientation of the thumbwheel housing 224 to the handle 222 orients the user with respect to the distal insertion head 230. The inserter shaft 228 is coupled to the thumbwheel 232 and is freely rotatable with low friction due to the spacer. The user may then employ the thumbwheel 232 to rotate the inserter shaft 228 thereby advancing it towards distal inserter head 230.

The elongate tubular element 226 is generally cylindrical and of a length sufficient to allow the device to span from the surgical target site to a location sufficiently outside the patient's body so the handle 222 and thumbwheel housing 224 can be easily accessed by a clinician or a complimentary controlling device. The elongate tubular element 226 is dimensioned to receive a spring 238 and the proximal end of the inserter shaft 228 into the inner bore of the elongate tubular element 226.

The distal inserter head 230 is comprised of a fixed inserter base 240 extending generally perpendicularly from elongate tubular element 226, an actuating member 242 extending generally perpendicularly from the inserter shaft 228, and two gripping arms 244.

Figure 34:
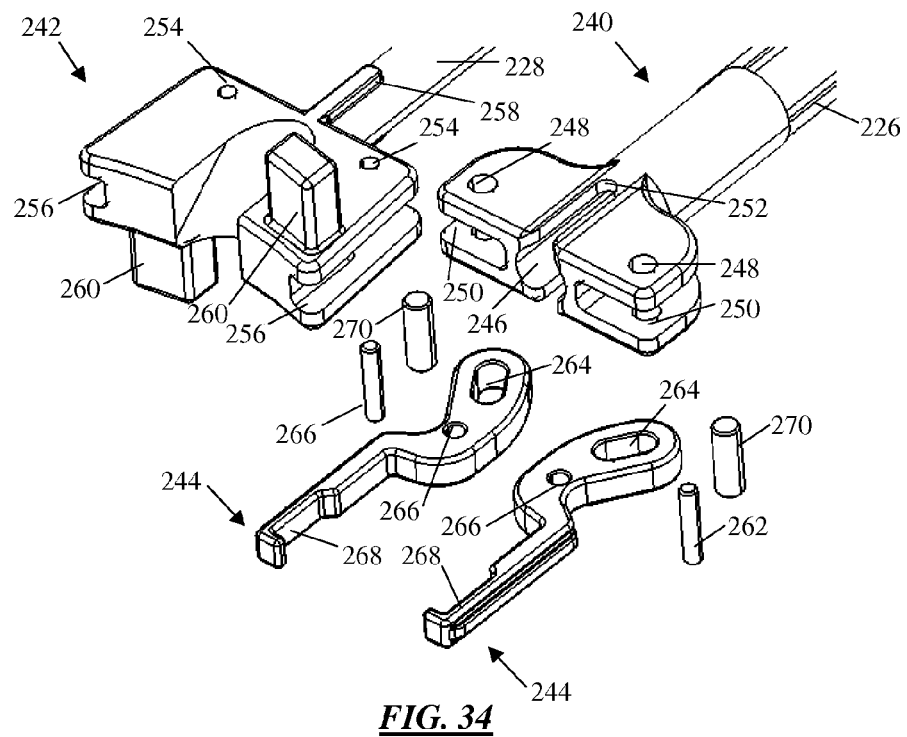
FIG. 34 is an exploded view of the insertion head of the insertion instrument of FIG. 32.
Figure 35:
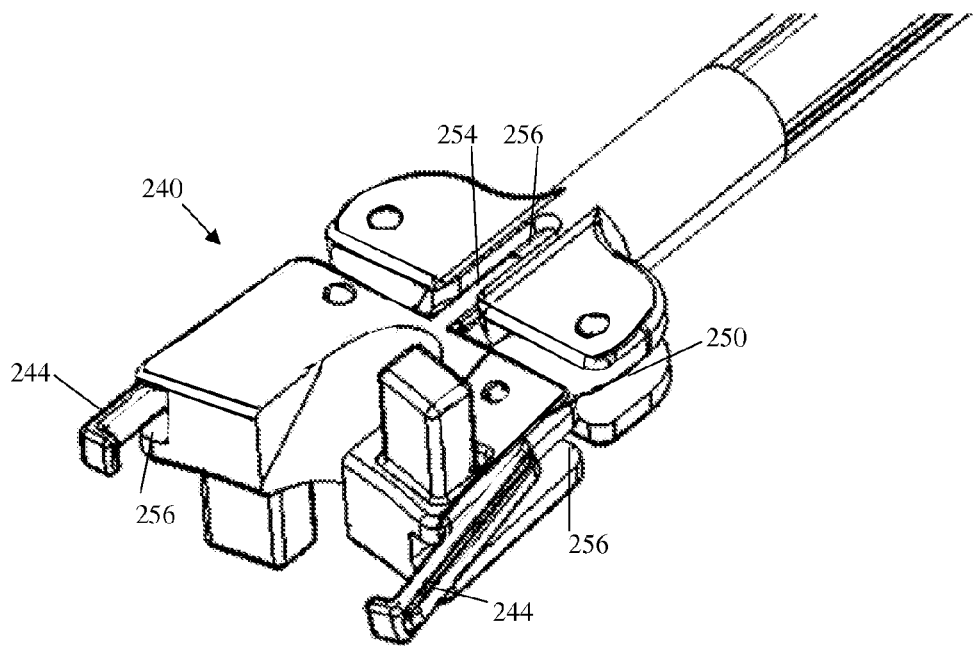
FIG. 35 is a perspective, detailed view of the insertion instrument of FIG. 32 with the gripping arms in an open position.
Figure 36:
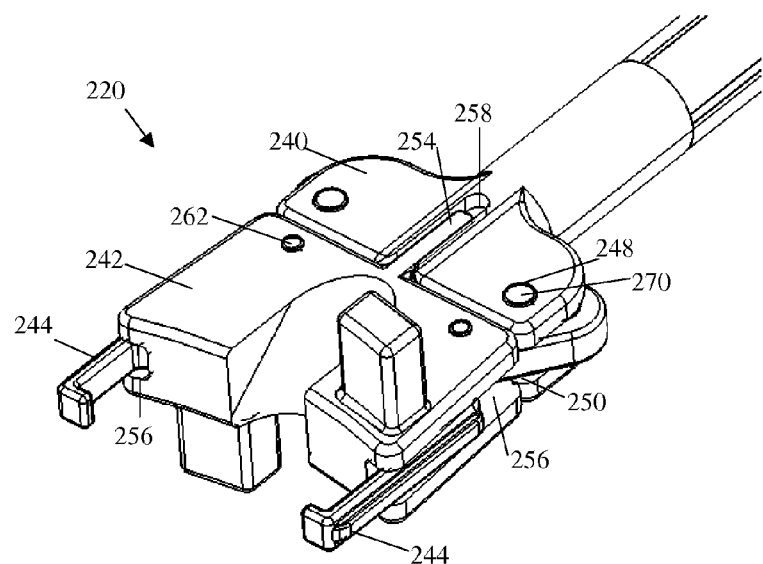
FIG. 36 is a perspective, detailed view of the insertion instrument of FIG. 32 with the gripping arms in a closed position.

As best viewed in FIGS. 34-36, the inserter base 240 contains a central aperture 246, two guide post apertures 248, two lateral channels 250, and a central slot 252. The central aperture 246 on the inserter base 240 is sized and dimensioned to allow slidable passage over the inserter shaft 228.

Actuating member 242 contains two pin-receiving apertures 254, two lateral channels 256 and a central protrusion 258. The pin-receiving apertures 254 are capable of receiving the pivot pins 262 centrally located on the gripping arms 244. This provides a fixed point for the gripping arm 244 to rotate around in relation to the actuating member 242. Each lateral channel 256 is sized and dimensioned such that the lateral aspect of each gripping arm 246 is seated within the lateral channel 256. The central protrusion 258 is sized and dimensioned to be slideably received by the central slot 252 on the inserter base 240. As the central protrusion 258 of the actuating member 242 is being advanced by the inserter shaft 236, it travels along the appropriate path within the central slot 252. Actuating member 242 may further contain at least one depth stop 260 which serves to limit the depth of insertion of the insertion instrument 220 into the disc space of the spine.

The two gripping arms 244 each contain laterally-disposed guide slots 264, a medially disposed pivot pin channel 266, and a terminal engagement hook 268. Gripping arms 244 are seated within the inserter base 240 via the lateral channels 250 and seated within the actuating member 242 via the lateral channels 256. Gripping arms 244 are attached to the actuating member 242 via the pivot pins 262 received within the pin-receiving apertures 254 on the actuating member 242. The gripping arms 244 are pivotably disposed within the fixed inserter base 240 via the guide posts 270 disposed within the guide slots 264 and the guide post apertures 248.

Figure 37:
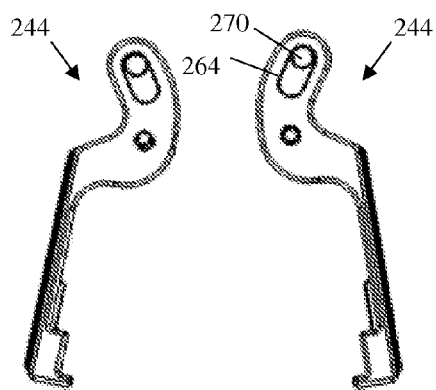
FIG. 37 shows the gripping arms in an open orientation.
Figure 38:
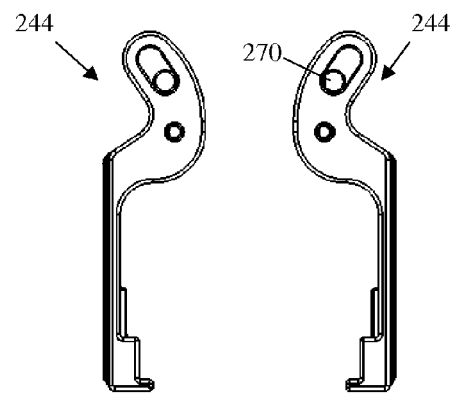
FIG. 38 shows the gripping arms in a closed position.
Figure 39:
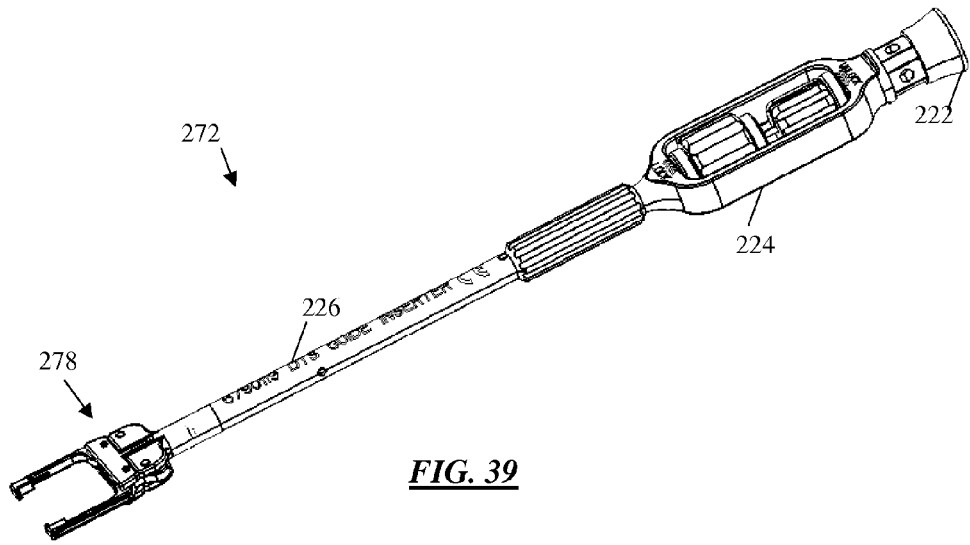
FIG. 39 is an insertion instrument according to a second embodiment.

As illustrated in FIG. 36, the initial position of the inserter shaft 228 is fully advanced such that the actuating member 242 is at a distance distal to the inserter base 240 and the guide posts 270 are placed in a first, proximal position within the guide slots 264 (FIG. 37). The gripping arms 244 may then be placed adjacent to the engagement grooves 32, 132 of the spinal fusion implant 10, 110, 210. The rotation of the thumbwheel 232 in the clockwise direction causes the inserter shaft 228 to retreat within the elongate tube member 226 which will result in pulling the actuating member 242 closer towards the inserter base 240. This movement will cause the gripping arms 244 to pivot about the pivot pins 262 of the gripping arms 244. The gripping arms 244 are then guided medially and proximally via the interaction of the guide posts 270 on the inserter base 240 within the guide slots 264 on the griping arms 244 towards the second, distal position (FIG. 38). When the inserter shaft 228 is fully retracted within the elongate tubular member 226, and the actuating member 242 has reached a final position with the inserter base 240 (as shown in FIG. 36), the gripping arms 244 are releaseably engaged to the engagement grooves 32, 132 of the spinal fusion implant 10, 110, 210 such that the insertion instrument 220 is stabilized relative to the special fusion implant 10, 110, 210. Once the implant 10, 110, 210 has been successfully inserted into the disc space, the thumbwheel 232 direction is reversed, thereby de-coupling the inserter 220 from the implant 10, 110, 210.

Figure 42:
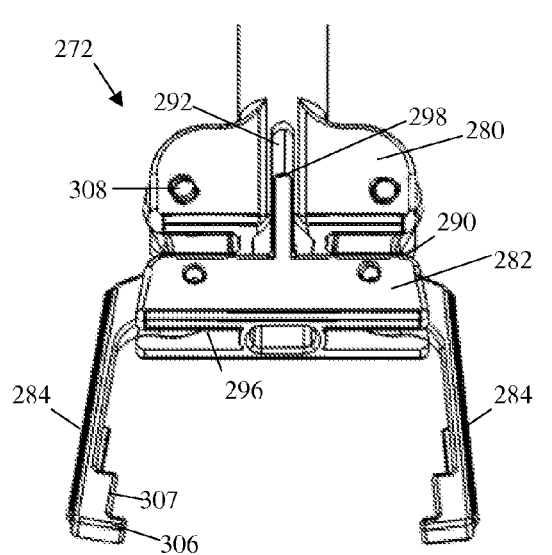
FIG. 42 is a perspective, detailed view of the insertion instrument of FIG. 39 with the gripping arms in an open position.
Figure 43:
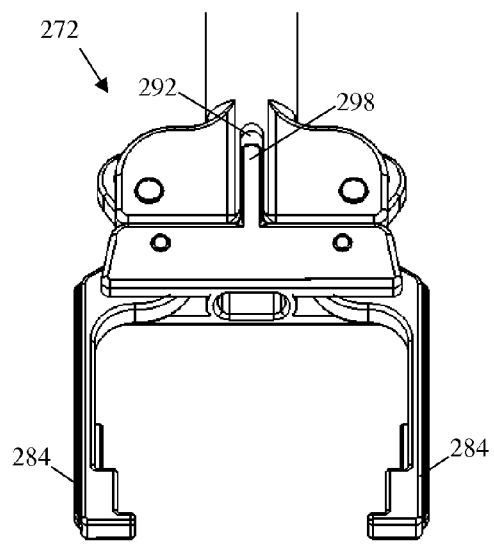
FIG. 43 is a perspective, detailed view of the insertion instrument of FIG. 39 with the gripping arms in a closed position.
Figure 44:
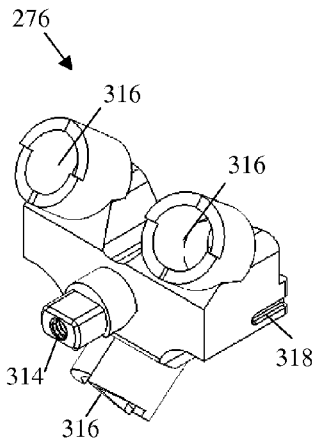
FIG. 44 is a perspective view of a screw guide attachment for use with the insertion instrument of FIG. 39.
Figure 45:
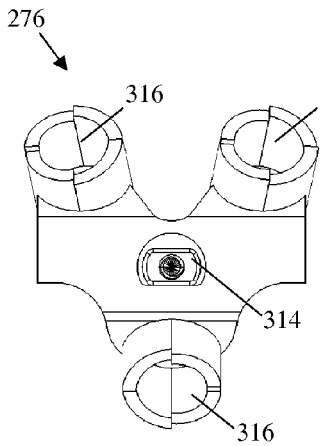
FIG. 45 is a front view of the screw guide attachment of FIG. 44.
Figure 46:
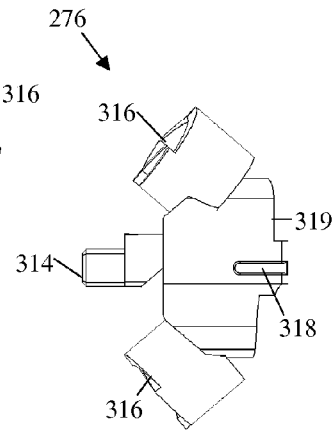
FIG. 46 is a side view of the screw guide attachment of FIG. 44.

FIGS. 39-46 detail an insertion instrument 272 according to a second embodiment of the present invention, preferably adapted for insertion from an anterior approach. The handle 222 is fixed to the thumbwheel housing 224 allowing easy handling by the user. By way of example, the thumbwheel housing 224 holds at least two thumbwheels: one thumbwheel 232 for tightening the gripping arms 244 and a second thumbwheel 274 for securing the screw guide attachment 276 (FIG. 44). The thumbwheel housing 224 further comprises at least two spacers 234. Because the handle 222 is fixed, the user has easy access to the thumbwheels 232, 274 and can stably turn the thumbwheel 232, 274 relative to the thumbwheel housing 224. Additionally, the relative orientation of the thumbwheel housing 224 to the handle 222 orients the user with respect to the distal insertion head 278. The inserter shaft 228 is attached to the thumbwheel 232 and is freely rotatable with low friction due to the spacer 232. The user may then employ the thumbwheel 232 to rotate the inserter shaft 228 to advance it towards distal inserter head 278. The inserter rod 310 is attached to the thumbwheel 274 and is freely rotatable with low friction due to the spacer 232. The user may also employ the thumbwheel 274 to rotate the inserter rod 310 to advance the threaded distal end 312 towards the threaded aperture 314 on the screw guide attachment 276.

The elongate tubular element 226 is generally cylindrical and of a length sufficient to allow the device to span from the surgical target site to a location sufficiently outside the patient's body so the handle 222 and thumbwheel housing 224 can be easily accessed by a clinician or a complimentary controlling device. The elongate tubular element 226 may be dimensioned to receive a spring (not shown) and the proximal end of the inserter shaft 228 into the inner bore of the elongate tubular element 226.

The distal inserter head 278 is comprised of a fixed inserter base 280 extending generally perpendicularly from elongate tubular element 226, an actuating member 282 extending generally perpendicularly from the inserter shaft 228 and two gripping arms 284.

Figure 41:
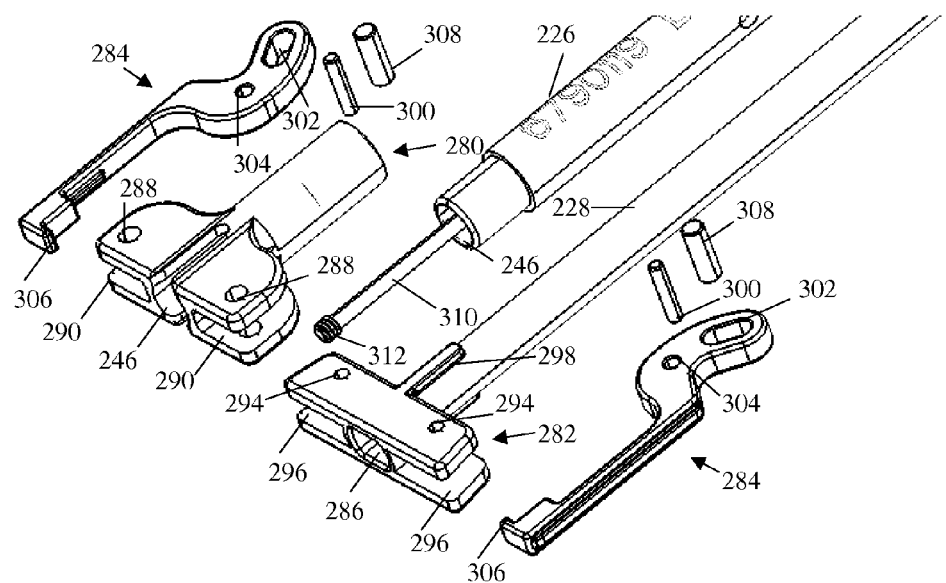
FIG. 41 is an exploded view of the insertion head of the insertion instrument of FIG. 39.

As best viewed in FIG. 41-43, the fixed inserter base 280 contains a central aperture 246, two guide post apertures 288, two lateral channels 290, and a central slot 292. The central aperture 246 on the inserter base 280 is sized and dimensioned to allow slidable passage over the inserter shaft 236.

Actuating member 282 contains two pin-receiving apertures 294, two lateral channels 296, a central aperture 286, and a central protrusion 298. The pin-receiving apertures 294 are capable of receiving the pivot pins 300 centrally located on the gripping arms 284. This provides a fixed point for the gripping arm 284 to rotate in relation to the actuating member 282. Each lateral channel 296 is sized and dimensioned such that the lateral aspect of each gripping arm 284 is seated within the lateral channel 296. The central protrusion 298 is sized and dimensioned to be slideably received by the central slot 292 on the inserter base 280. As the central protrusion 298 of the actuating member 282 is advanced by the inserter shaft 228, it travels along the appropriate path within the central slot 292.

The two gripping arms 284 each contain laterally-disposed guide slots 302, a medially disposed pivot pin channel 304, and a terminal engagement hook 306. Gripping arms 284 are seated within the inserter base 280 via the lateral channels 290 and seated within the actuating member 282 via the lateral channels 296. Gripping arms 284 are attached to the actuating member 282 via the pivot pins 300 received within the pin-receiving apertures 294 on the actuating member 282. The gripping arms 284 are pivotably disposed within the fixed inserter base 280 via the guide posts 308 disposed within the guide slots 302 and the guide post apertures 288.

As illustrated in FIG. 42, the initial position of the inserter shaft 228 is fully advanced such that the actuating member 282 is at a distance distal to the inserter base 280 and the guide posts 308 are placed in a first, distal position within the guide slots 302. The gripping arms 284 may then be placed adjacent to the engagement grooves 32, 132 of the spinal fusion implant 10, 110, 210. The rotation of the thumbwheel 232 in the clockwise direction causes the inserter shaft 228 to retreat within the elongate tube member 226 which will result in pulling the actuating member 282 closer towards the inserter base 280. This movement will cause the gripping arms 284 to pivot about the pivot pins 300 of the gripping arms 284. The gripping arms 284 are guided medially and proximally via the guide slots 302 on the inserter base 280 towards the second, proximal position. When the inserter shaft 228 is fully retracted within the elongate tubular member 226 and the actuating member 282 has reached a final position with the inserter base 280 (as shown in FIG. 43), the gripping arms 284 are releaseably engaged to the engagement grooves 32, 132 of the spinal fusion implant 10, 110, 210 such that the insertion instrument 272 is stabilized relative to the special fusion implant 10, 110, 210. Once the implant 10, 110, 210 has been successfully inserted into the disc space, the thumbwheel 232 direction is reversed, thereby de-coupling the inserter 220 from the implant 10, 110, 210.

Figure 40:
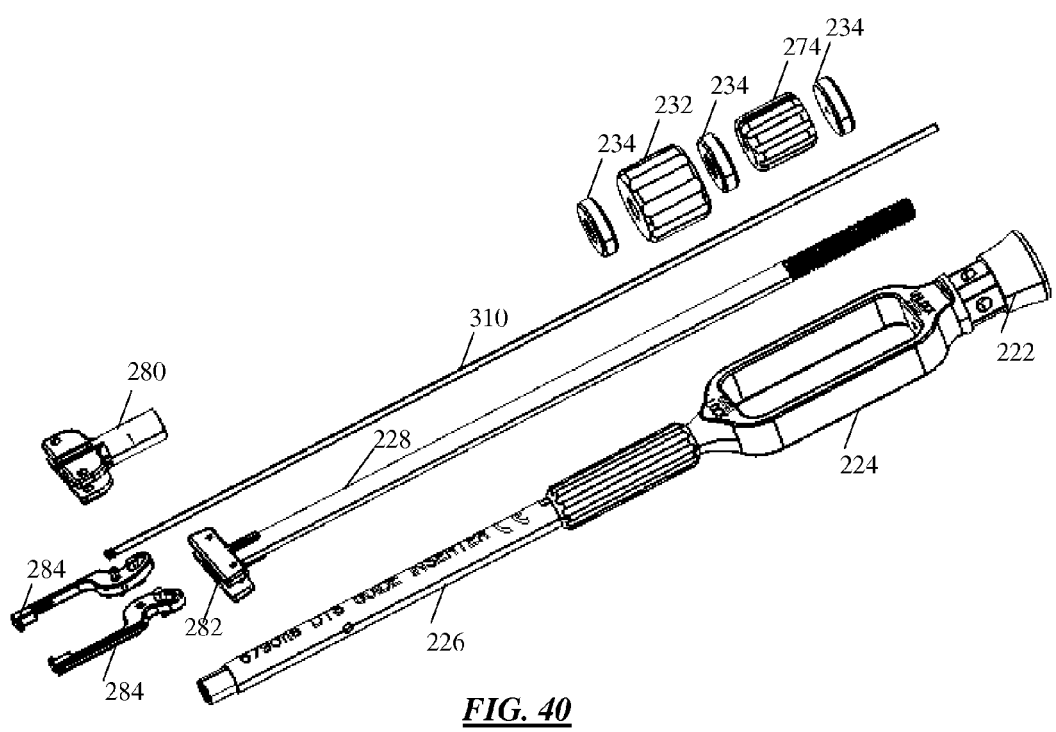
FIG. 40 is an exploded view of the insertion instrument of FIG. 39.

As shown in FIGS. 40 and 41, the insertion rod 310 is centrally disposed within the elongate tubular element 226 and inserter shaft 228 such that its threaded distal end 312 passes through the central aperture 246 of the fixed inserter base 280 and the central aperture 286 of the inserter shaft 228. The threaded distal end 312 of the insertion rod 310 may be threadably coupled to the screw guide attachment 276 shown in FIGS. 44-46. The screw guide attachment 276 comprises a medially disposed threaded aperture 314 for threadably receiving the threaded distal end 312 of the insertion rod 310 as well as three screw guide holes 316 sized, dimensioned and positioned over the screw holes 22, 24, or 122, 124 whereby drivers, including the drivers of FIGS. 59-62 may be used. The screw guide attachment 276 is configured with a slot 318 that mating engages with the elongated portion 307 of the terminal engagement hook 306. The posterior side 20, 120, 220 of the spinal implant 10, 110, 210 is inserted between the gripping arms 284 such that the posterior side 20, 120, 220 is engaged with the distal side 319 of the screw guide attachment 276. The elongated portion 207 of the gripping arm 284 secures the screw guide attachment 276 and the terminal engagement hook secures the spinal implant 10, 110, 210. The second thumbwheel extends the insertion rod 310 such that the screw guide attachment 276 is positioned securely against the spinal implant 10, 110, 210, and is held firmly in place by the engagement of the slot 318 with the elongated portion 307 and the terminal engagement hook 306 with the engagement grooves 32, 132. Once the implant 10, 110, 210 has been successfully inserted into the disc space, the screws 26, 126 may be placed using the screw guide attachment 276 and the drivers 350, 352, 354, 356. Following placement of the implant and screws, the thumbwheel 234, 278 directions are reversed, thereby de-coupling the inserter 220 from the implant 10, 110, 210.

Figure 47:
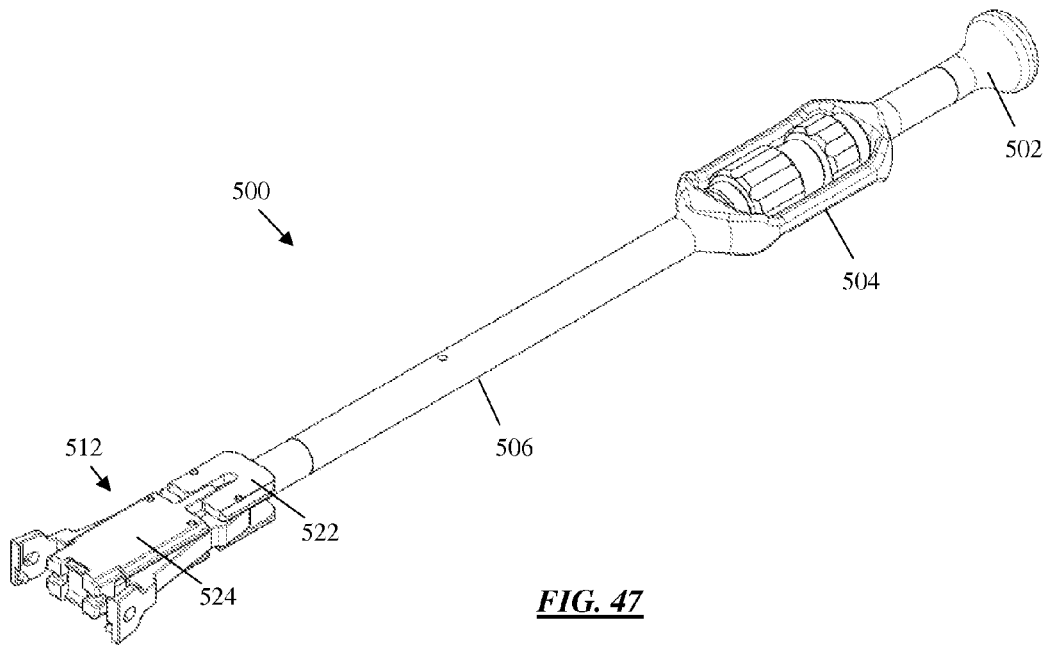
FIG. 47 is a perspective view of an insertion instrument according to a third embodiment.
Figure 48:
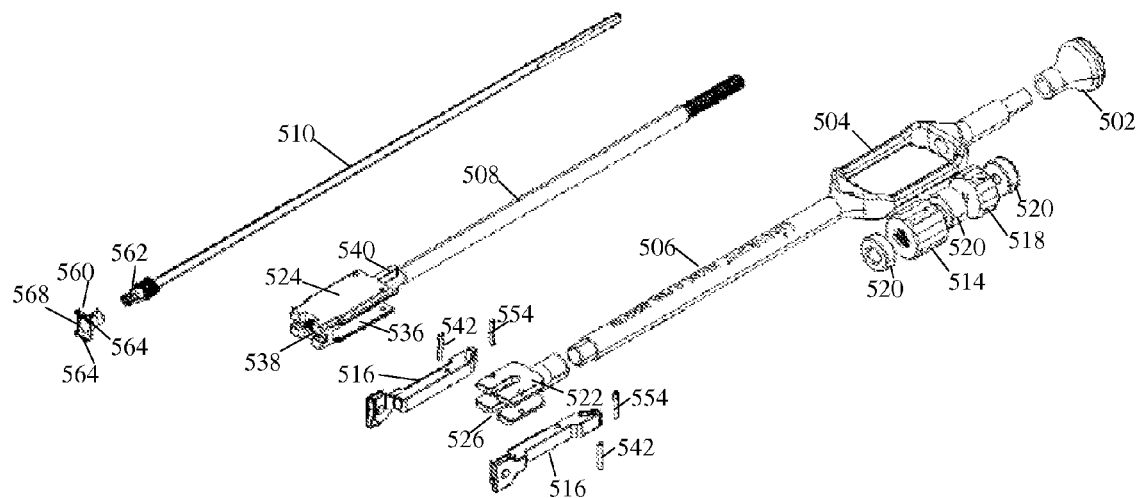
FIG. 48 is an exploded view of the insertion instrument of FIG. 47.

FIGS. 47-53 detail an insertion instrument 500 according to a third embodiment of the present invention, preferably adapted for insertion of a multi-part implant 400 from an anterior approach. According to a broad aspect, the insertion instrument 500 includes a handle 502, a thumbwheel housing 504, and elongate tubular element 506, an inserter shaft 508, an inner rod 510, and a distal inserter head 512, as illustrated in FIGS. 47-48.

The handle 502 is generally disposed at the proximal end of the insertion instrument 500. The handle 502 may be adapted to receive a striking force. The handle 502 is fixed to the thumbwheel housing 504 allowing easy handling by the user. By way of example, the thumbwheel housing 504 holds at least two thumbwheels: one thumbwheel 514 for tightening the gripping arms 516 and a second thumbwheel 518 for advancing the inner rod 510. The thumbwheel housing 504 further comprises at least two spacers 520. Because the handle 502 is fixed, the user has easy access to the thumbwheels 514, 518 and can stably turn the thumbwheels 514, 518 relative to the thumbwheel housing 504. The thumbwheel housing 504 may additionally have side portions which are narrowed. The narrowed side portions of the thumbwheel housing 504 allows the user greater surface area for accessing the thumbwheels 514, 518. Additionally, the relative orientation of the thumbwheel housing 504 orients the user with respect to the orientation of the distal inserter head 512. The inserter shaft 508 is attached to the first thumbwheel 514 and is freely rotatable with low friction due to the spacer. The user may employ the first thumbwheel 514 to rotate the inserter shaft 508 thereby engaging the distal inserter head 512. The user may employ the second thumbwheel 518 to rotate the inner rod 510 thereby engaging the anterior side 408 of the multi-part implant 400 to maintain proper alignment of the lower cover plate 402 and upper cover plate 406 during insertion of the multi-part implant 400 in the intervertebral disc space.

The thumbwheels 514, 518 may also be configured with surface texturing such as with ridges or knurling for easier rotation by the user. The thumbwheels 514, 518 may also be dimensioned with different sizes or marked with numbering or lettering to indicate the order of deployment. For example, the first thumbwheel 514 may be larger and/or marked with the number 1, and the second thumbwheel 518 may be smaller and/or marked with the number 2.

The elongate tubular member 506 is generally cylindrical and of a length sufficient to allow the device to span from the surgical target site to a location sufficiently outside the patient's body so the handle 502 and thumbwheel housing 504 can easily be accessed by a clinician or a complimentary controlling device. The elongate tubular element 506 is dimensioned to receive the proximal end of the inserter shaft 508 into the inner bore of the elongate tubular member 506.

The distal inserter head 512 is comprised of a fixed inserter base 522 extending generally perpendicularly from the elongate tubular member 506, and actuating member 524 extending generally perpendicularly from the from the inserter shaft 508, and two gripping arms 516.

Figure 49:
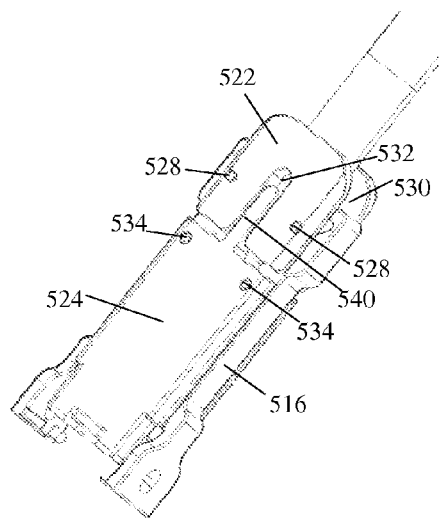
FIG. 49 is a perspective, detailed view of the distal insertion head of the insertion instrument of FIG. 47.
Figure 54:
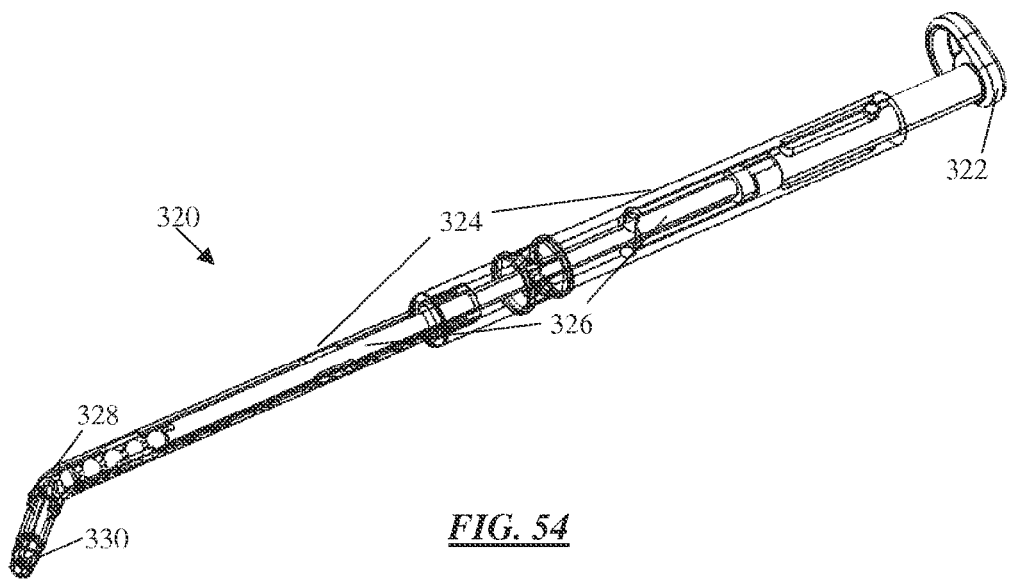
FIG. 54 is a perspective view of a retractable, angled awl according to a preferred embodiment.
Figure 55:
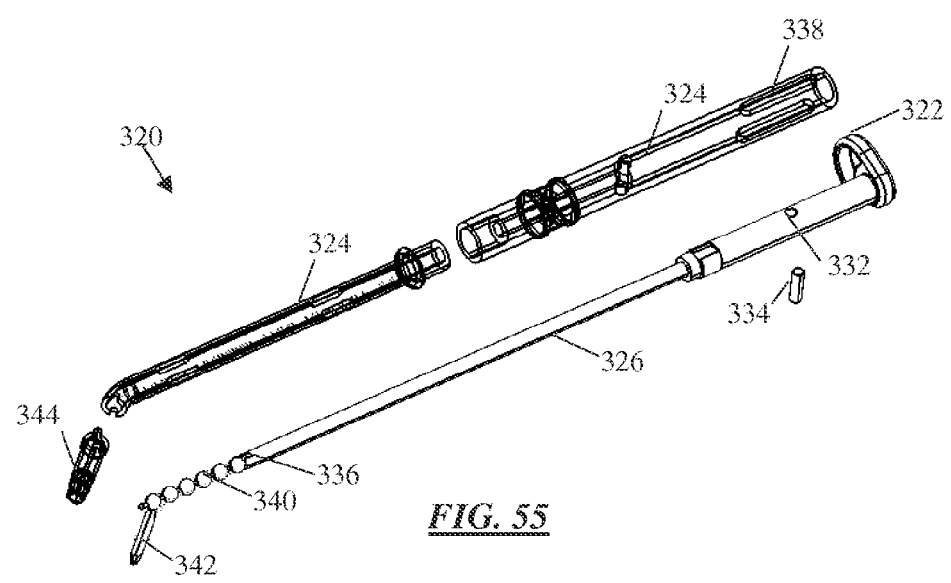
FIG. 55 is an exploded view of the retractable, angled awl of FIG. 54.
Figure 56:
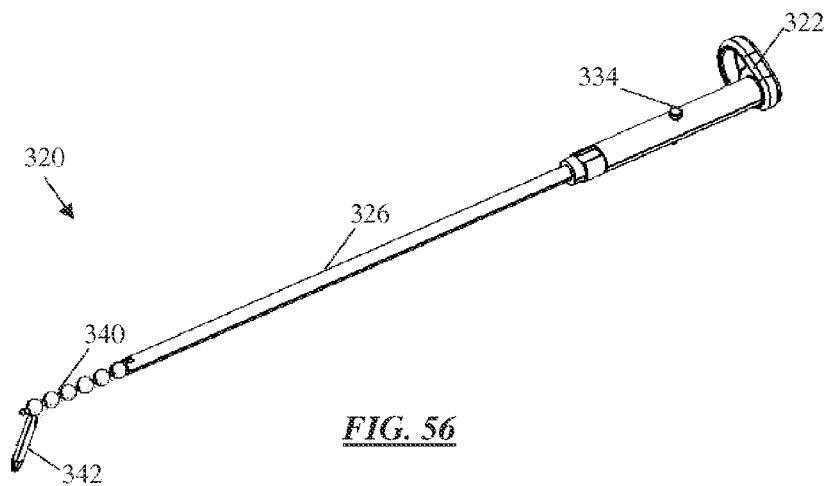
FIG. 56 is a perspective view of the retractable, angled awl of FIG. 54 with the cover removed.
Figure 57:
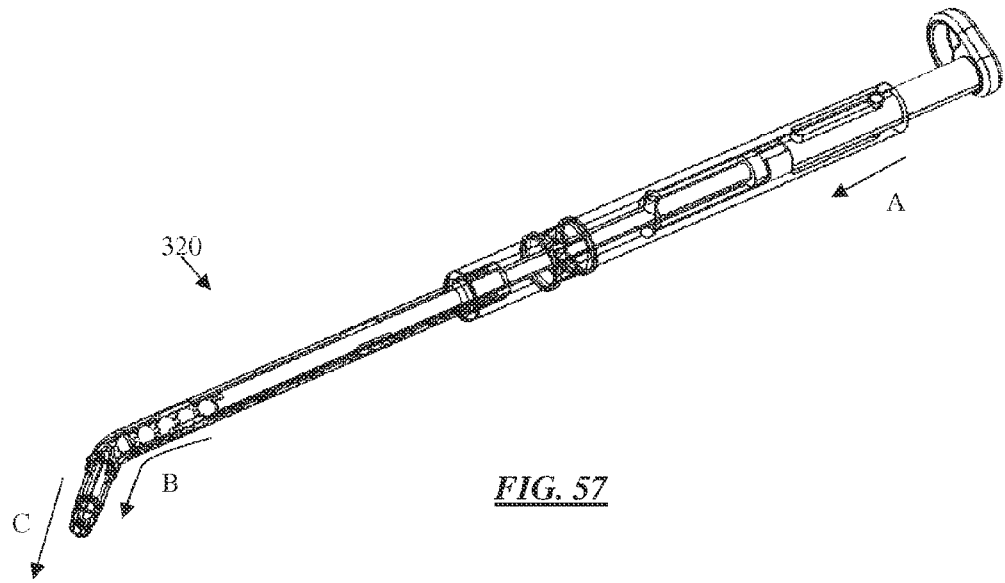
FIG. 57 is a perspective view of the retractable, angled awl of FIG. 54 with arrows indicating the movement of the retractable, angled awl.
Figure 58:
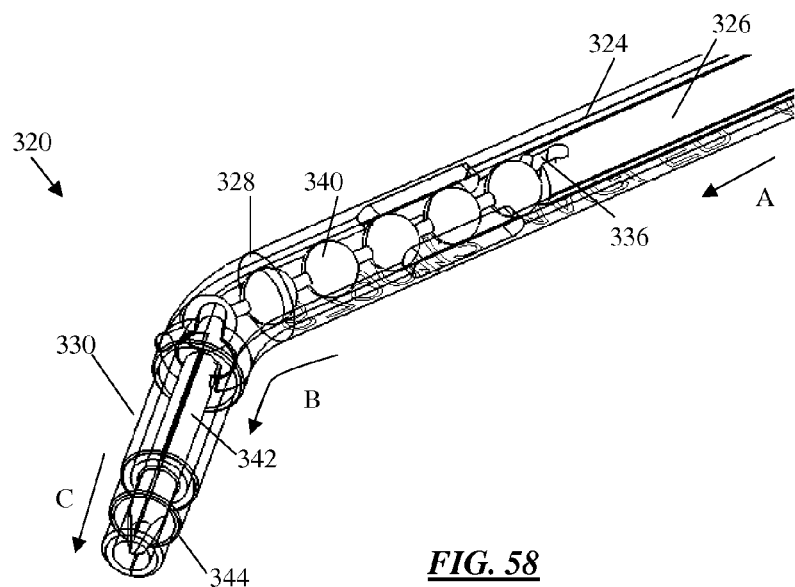
FIG. 58 is an exploded view of the movement of retractable, angled awl depicted in FIG. 57.

As best viewed in FIGS. 48-49, the fixed inserter base 522 contains a central aperture 526, two guide post apertures 528, two lateral channels 530, and a central slot 532. The central aperture 532 on the fixed inserter base 522 is sized and dimensioned to allow slidable passage over the inserter shaft 508.

Actuating member 524 contains two pin-receiving apertures 534, two lateral channels 536, a central aperture 538, and a central protrusion 540. The pin-receiving apertures 534 are capable of receiving the pivot pins 542 centrally located in the gripping arms 516. This provides a fixed point for the gripping arms 516 to rotate in relation to the actuation member 524. Each lateral channel 536 is sized and dimensioned such that the lateral aspect of each gripping arm 516 is seated within the lateral channel 536. The central protrusion 540 is sized and dimensioned to be slideably received by the central slot 532 of the fixed inserter base 522. As the central protrusion 540 of the actuating member 524 is advanced by the inserter shaft 508, it travels along the appropriate path within the central slot 532. The actuating member 524 may also be provided with a midline marker (not shown) centrally disposed along the longitudinal axis to assist the clinician with placement of the multi-part implant 400.

The two gripping arms 516 each contain laterally-disposed guide slots 544, a medially disposed pivot pin aperture 548, and terminal engagement prongs 550, 552. Gripping arms 516 are seated within the fixed inserter base 522 via the lateral channels 530 and seated within the actuating member 524 via the lateral channels 536. Gripping arms 516 are attached to the actuating member 524 via the pivot pins 542 received within the pin-receiving apertures 534 on the actuating member 524. The gripping arms 244 are pivotably disposed within the fixed insert base 522 via the guide posts 554 disposed with the laterally-disposed guide slots 544 and the guide post apertures 528. As shown in FIG. 50, the terminal engagement prongs 550, 552 are configured to correspond and mate with the arrangement of the slot 418 and aperture 420 of the multi-part implant 400. The terminal engagement prong 550 is preferentially configured as a elongated prong, and the terminal engagement prong 552 is preferentially configured as a circular prong. It is contemplated that many configurations of engagement prongs and recessed engagement structures could be envisioned to hold the multi-part implant 400 in the insertion instrument 500.

The gripping arms 516 have other features that assist with the docking and visualization of the multi-part implant 400. The gripping arms have a shoulder portion 556 to assist with docking that rises up along the length of the elongated engagement prong 550. The shoulder portion 556 guides the elongated engagement prong 550 such that the elongated engagement prong 550 preferentially engages first into position within the recessed slot 418. This ensures that the majority of the compression force is applied across the elongated engagement prongs 550 and through the multi-part implant 400 to hold the multi-part implant 400 securely in the insertion instrument 500. The circular prong 552 engages secondarily and is also held securely by the compression force of the gripping arms about the multi-part implant 400. To assist with visualization, the gripping arms 516 have a visualization aperture 558 positioned near the distal end of the gripping arms 516. The visualization aperture 558 allows the clinician to determine the positioning and extent of the multi-part implant 400 when viewed with a lateral X-ray. The visualization aperture 558 allows the clinician to readily discern the edge of the anterior side 408 of the multi-part implant 400 from the insertion instrument 500.

As shown in FIG. 48, the inner rod 510 is centrally disposed within the inserter shaft 508 and elongate tubular element 506 such that distal pusher tip 560 extends beyond the central aperture 538 of the inserter shaft 508. The distal pusher tip 560 of the inner rod 510 engages against the anterior side 408 of the multi-part implant 400.

As shown in sectional view in FIG. 52, the distal end of the inner rod 510 is configured with a projection 562 that is notched and slotted for mounting the distal pusher tip 560. The distal pusher tip 560 snaps over the projection 562 and is held surely in place by the notch. As best shown in FIG. 48, the distal pusher tip 560 is configured with a pair of raised outer edges 564 that are spaced apart and parallel to one another and a central channel 566. The raised outer edges 564 press against and contact the multi-part implant 400 along the anterior side 408 of the lower cover plate 402 and upper cover plate 406, rather than the articulating implant core 404. The raised outer edges 564 apply pressure to the cover plates to maintain the assembled multi-part implant 400 in the proper alignment for insertion. The central channel 566, when viewed from the side with a lateral X-ray, cooperates with the visualization apertures 558 on the gripping arms 516 to enable visualization of the multi-part implant 400. The user is readily able to discern the anterior side 408 of the multi-part implant 400 from the distal pusher tip 560 of the insertion instrument 500.

The distal pusher tip 560 fits into a distal notch 568 of the actuating member 524. The distal notch 566 maintains the distal pusher tip 560 in proper alignment to engage the multi-part implant 400 during rotation of the second thumbwheel 518.

As illustrated in FIG. 47, the initial position of the inserter shaft 508 is fully advanced such that the actuating member 524 is at a distance distal to the fixed inserter base 522 and the guide posts 554 are placed in a first, proximal position (open) within the laterally-disposed guide slots 544. The gripping arms 516 are then be placed adjacent the recessed engagement structures 418, 420 of the multi-part implant 400, taking care to orient the matching elongated prongs 550 with the recessed slots 418 and the circular prongs 552 with the recessed apertures 420. The rotation of the first thumbwheel 514 in the clockwise direction causes the inserter shaft 508 to retreat within the elongate tubular member 506 which will result in pulling the actuating member 524 toward the fixed insert base 522. This movement will cause the gripping arms 516 to pivot about the pivot pins 542 disposed within the pivot pin apertures 548 of the gripping arm 516. The gripping arms 516 are then guided medially and proximally by the guide posts 554 connected to the fixed inserter base 522 via the laterally-disposed guide slots 544 of the gripping arms 516 towards the second, distal position (closed). The projection 540 of the actuating member 524 resists rotation of the inserter shaft 508 and allows the actuating member 524 to longitudinally retreat within the slot 532 of the fixed inserter base 522 without twisting or otherwise coming out of alignment with the insertion instrument 500. When the inserter shaft 508 is fully retracted within the elongate tubular member 506, and the actuating member 524 has reached a final position with the fixed inserter base 522, the gripping arms 516 are releasably engaged with the recessed engagement structures 418, 420 of the multi-part implant 400.

The rotation of the second thumbwheel 518 in the clockwise direction causes the inner rod 510 to extend from the actuating member 524 which will result in the distal pusher tip 560 applying pressure against the multi-part implant 400. This engagement of the distal pusher tip 560 against the multi-part implant 400 maintains the proper alignment of the multi-part implant during insertion and prevents the lower cover plate 502 and upper cover plate 506 of the multi-part implant 400 from separating or becoming misaligned. The multi-part implant 400 is stabilized relative to the insertion instrument 500.

The mounted multi-part implant 400 is then positioned in the prepared intervertebral disc space. A slight tapping or hammering on the handle 502 may also be applied to assist with the positioning of the multi-part implant 400. Final positioning is confirmed with X-ray imaging. To assist with visualization of the anterior extent of the multi-part implant 400 a rectangular slot 570 will appear (see FIG. 53B) when imaged with a lateral view X-ray. The visualization apertures 558 on the gripping arms 516 align with the central channel 568 of the distal pusher tip 560 permitting the user to discern the anterior side 508 of the multi-part implant 400 from the insertion instrument 500. After final placement is confirmed, the first thumbwheel 514 direction is reversed, thereby decoupling the insertion instrument 500 from the multi-part implant 400. The multi-part implant 400 is fixed in the intervertebral disc space by press-fit of the teeth and biological fixation of the cover plates.

The present invention further provides an awl for forming one or more pilot holes in the superior and inferior vertebral bodies to receive bone screws 26, 126. According to a broad aspect of one embodiment, a retractable, angled awl instrument 320 is comprised of a handle 322, an elongate shaft 324, an advancement shaft 326, a transition region 328, and a driver region 330 (FIGS. 54-58).

The handle 322 is generally disposed at the proximal end of the instrument 320. The handle 322 may be further equipped with a universal connector to allow the attachment of accessories for ease of handling of the instrument (e.g. a straight handle, or a T-handle, not shown). The advancement shaft 326 extends from handle 322. The advancement shaft is generally cylindrical and of a length sufficient to allow the device to span from the surgical target site to a location sufficiently outside the patient's body so the handle 322 can be easily accessed by a clinician or complimentary controlling device. The advancement shaft 326 is comprised of a pin channel 332 for receiving pin 334 and a distal end 336 adapted to interface with the proximal end of the bead chain linkages 340.

The elongate shaft 324 is generally cylindrical and of a length sufficient to allow the device to span from the surgical target site to a location sufficiently outside the patient's body so the handle 322 can be easily accessed by a clinician or a complimentary controlling device. The elongate tubular shaft 324 is dimensioned to receive the advancement shaft 326 as well as the proximal end of the cover 344. The proximal end of the elongate shaft 324 is configured with a pin slot 338 that guides the pin 334 and the advancement shaft 326 in the direction of arrow A.

Transition region 328 contains a plurality of bead chain linkages 340 hingedly linking the advancement shaft 326 to the awl tip 342. The driver region 330 is composed of an awl tip 342 and a distal cover 344.

In use, the distal end of the instrument 320 is placed within the screw hole 122, 124. The diameter of the cover 344 bottoms out on the ledge 138 of the screw hole 122, 124, thereby acting as a guide for pilot hole preparation. The handle 322 is used to depress the advancement shaft 326 along the path of the pin slot 338 on the elongate shaft 324 thereby directing movement in the direction of arrow A. After the cover 344 bottoms out, the bead chain linkages 340 move in the direction of arrow B within the transition region 328 in between the elongate shaft 324 and the cover 344. This movement of the bead chain linkages 340 along the arrow B directs movement of the awl tip 342 in the direction of arrow C. Thus, the awl tip 342 may be used to form pilot holes in line with the axis of the screw hole 122, 124.

FIGS. 59-62 further illustrate a plurality of drivers for use with the present invention thereby providing the user with a host of options for securing the bone screws 126. According to a broad aspect, the drivers may be comprised of an elongate shaft portion 302 coupled to a distal driving portion 304.

Figure 59:
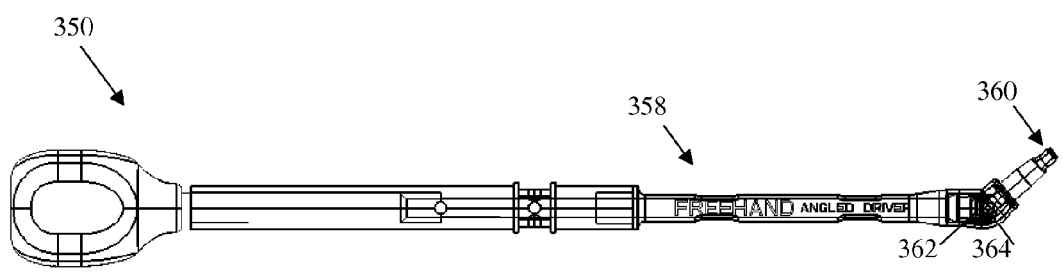
FIG. 59 is an angled driver according to a first embodiment.
Figure 60:
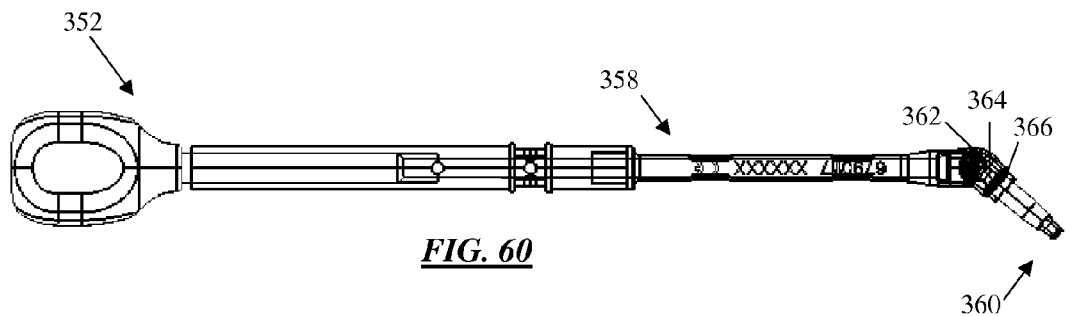
FIG. 60 is an angled driver according to a second embodiment.

According to one embodiment, the driver 350 may include an elongate shaft portion 358 hingedly coupled to a distal driving portion 360 via a universal joint 362 that engages the screw at a variety of angles (for example, the drivers shown in FIGS. 59-60). According to a second embodiment, the driver 350 may be provided with a sleeve 364 to prevent wrapping of tissue during use. Use of the sleeve 364 allows the driver 350 to engage the screw 126 at a fixed angle of preferably 60 degrees and further allows for more torque to be applied, should patient anatomy or surgeon preference so require. According to a third embodiment shown in FIG. 60, the driver 352 may be further provided with a cover 366. As the distal end of the driver 352 is placed within the screw hole 122, 124, the diameter of the cover 366 bottoms out on the ledge 138 of the screw hole 122, 124 thereby acting as a guide for screw placement.

Figure 61:
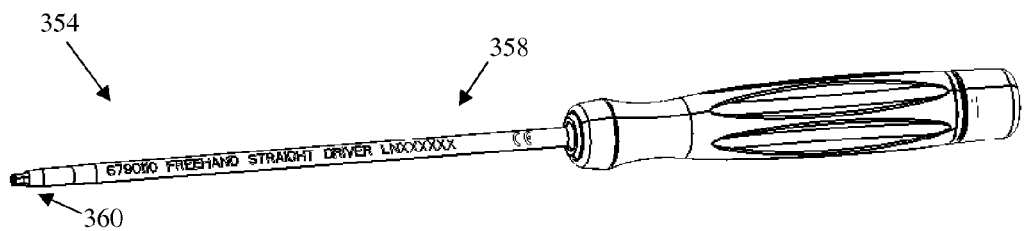
FIG. 61 a straight driver according to a first embodiment.
Figure 62:
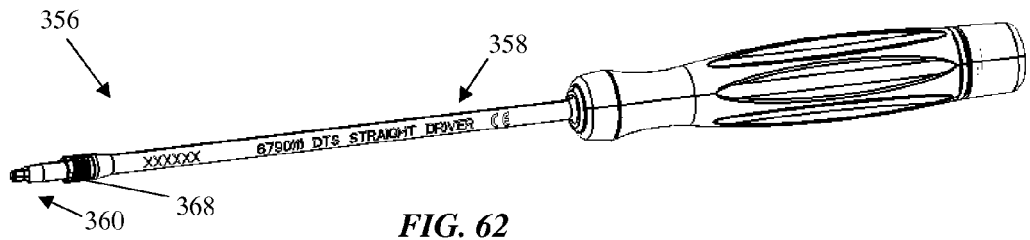
FIG. 62 is a straight driver according to a second embodiment.

As shown in FIG. 61, a straight driver 354 may also be provided. According to a second embodiment shown in FIG. 62, a guide cover 368 may be provided on the driving portion 360 of the straight driver 356. As the distal end of the driver 352 is placed within the screw hole 122, 124, the diameter of the cover 368 bottoms out on the ledge 138 of the screw hole 122, thereby acting as a guide for screw placement.

What is claimed is:

1. A spinal fusion implant, comprising:
a body configured for implantation between a superior and an inferior vertebra, having a top surface and a bottom surface, an anterior height and a posterior height, and a fusion aperture defined by an anterior wall, a posterior wall, and first and second lateral walls;
a plurality of fastener apertures extending through the anterior wall at oblique angles relative to a horizontal axis, each of said fastener apertures dimensioned to receive a bone fastener for insertion into one of the superior or inferior vertebrae, said bone fastener having a head, a shank and a collar disposed between said head and said shank;
wherein said plurality of fastener apertures have an anterior diameter and a posterior diameter, wherein said anterior diameter is greater than said posterior diameter; and
wherein said plurality of fastener apertures each comprise an annular groove dimensioned to retain the head of the bone fastener therein and a washer disposed within the annular groove, wherein each of the fastener apertures further includes a visualization marker on an exterior facing surface of the fastener aperture proximally adjacent the annular groove, said visualization marker configured to be obscured by the bone fastener during insertion of the bone fastener into the body and wholly visible on the exterior-facing surface of the fastener aperture when the bone fastener is fully inserted into the body.

2. The spinal fusion implant of claim 1, wherein the body is constructed of radiolucent, non-bone material.

3. The spinal fusion implant of claim 1, wherein said washer includes at least one surface having friction surface features.

4. The spinal fusion implant of claim 1, wherein the anterior height of the body is greater than the posterior height, such that the top surface of the body is oblique to the horizontal axis, such that the top surface creates a posterior-to-anterior angle relative to the horizontal axis.

5. The spinal fusion implant of claim 4, wherein said posterior-to-anterior angle is about 5°.

6. The spinal fusion implant of claim 1, wherein the oblique angles relative to the horizontal axis are between 25° and 50°.

7. The spinal fusion implant of claim 6, wherein the oblique angles relative to the horizontal axis are 40°.

8. The spinal fusion implant of claim 1, wherein said plurality of fastener apertures extend through the anterior wall at angles oblique to a longitudinal axis.

9. The spinal fusion implant of claim 8, wherein the oblique angles relative to the longitudinal axis are between 5° and 15°.

10. The spinal fusion implant of claim 1, wherein the plurality of fastener apertures is equal to three.

11. The spinal fusion implant of claim 1, wherein at least two of the fastener apertures are dimensioned to receive the bone fastener for insertion into the inferior vertebrae.

12. The spinal fusion implant of claim 1, wherein at least one of the top surface and bottom surface includes anti-migration features.

13. The spinal fusion implant of claim 1, wherein the body includes at least one radiopaque marker.

14. The spinal fusion implant of claim 1, wherein the body further comprises an engagement groove in the first and second lateral sides dimensioned to receive a gripping element of an inserter instrument.

\* \* \* \* \*